US011670410B1

(12) United States Patent
Robinson et al.

(10) Patent No.: US 11,670,410 B1
(45) Date of Patent: Jun. 6, 2023

(54) SYSTEMS AND METHODS TO AUTOMATICALLY ADMINISTER A PSYCHOACTIVE SUBSTANCE TO AN AIRWAY OF A USER BASED ON A DETECTED EVENT OR CONDITION

(71) Applicant: Green Sky Creations, LLC, Seattle, WA (US)

(72) Inventors: Simon Robinson, Seattle, WA (US); Brad Douglass, Black Diamond, WA (US)

(73) Assignee: Green Sky Creations LLC, Seattle, WA (US)

( * ) Notice: Subject to any disclaimer, the term of this patent is extended or adjusted under 35 U.S.C. 154(b) by 0 days.

(21) Appl. No.: 17/720,175

(22) Filed: Apr. 13, 2022

(51) Int. Cl.

| | |
|---|---|
| ***G16H 20/17*** | (2018.01) |
| ***A61B 5/11*** | (2006.01) |
| ***A61B 5/00*** | (2006.01) |
| ***G16H 20/10*** | (2018.01) |
| *A61M 11/00* | (2006.01) |

(52) U.S. Cl.

CPC ............... *G16H 20/17* (2018.01); *A61B 5/11* (2013.01); *A61B 5/4806* (2013.01); *A61B 5/4839* (2013.01); *A61B 5/6801* (2013.01); *G16H 20/10* (2018.01); *A61M 11/00* (2013.01)

(58) Field of Classification Search

CPC ....... A61B 5/4806; A61B 5/4839; A61B 5/11; A61B 5/6801; A61M 11/00; G16H 20/10; G16H 20/17

See application file for complete search history.

(56) References Cited

U.S. PATENT DOCUMENTS

| | | | | |
|---|---|---|---|---|
| 4,117,146 | A * | 9/1978 | Abdallah | A61K 31/415 514/392 |
| 5,335,657 | A * | 8/1994 | Terry, Jr | A61N 1/36017 607/45 |
| 5,510,381 | A * | 4/1996 | Pande | A61K 31/195 514/561 |
| 6,245,021 | B1 * | 6/2001 | Stampfer | A61B 5/165 607/45 |
| 6,356,784 | B1 * | 3/2002 | Lozano | A61N 1/36067 604/522 |
| 9,072,870 | B2 * | 7/2015 | Wu | A61B 5/318 |
| 9,084,797 | B2 * | 7/2015 | Caufriez | A61P 25/00 |

(Continued)

FOREIGN PATENT DOCUMENTS

WO WO2008116165 A2 9/2009

OTHER PUBLICATIONS

Bakker, Charlotte, et al. "Safety, pharmacokinetics, and pharmacodynamics of Gln-1062, a prodrug of galantamine." Alzheimer's & Dementia: Translational Research & Clinical Interventions 6.1 (2020): e12093. (Year: 2020).*

(Continued)

*Primary Examiner* — Nilay J Shah

(74) *Attorney, Agent, or Firm* — C. Rachal Winger; Lee & Hayes PC

(57) ABSTRACT

Described herein are systems and methods for automatically administering a psychoactive substance to a user based on detection of an event or condition during sleep. The systems and methods can be used to promote wellness in personal and research settings, and to facilitate brain-computer interface training, among other beneficial uses.

13 Claims, 8 Drawing Sheets

(56) References Cited

U.S. PATENT DOCUMENTS

| | | | | |
|---|---|---|---|---|
| 10,080,851 | B2 | 9/2018 | Davidson et al. | |
| 10,500,354 | B2 | 12/2019 | Newberry | |
| 10,688,190 | B2 | 6/2020 | Naheed | |
| 2002/0037533 | A1* | 3/2002 | Civelli | G01N 33/74 435/7.1 |
| 2004/0072900 | A1* | 4/2004 | Artman | A61P 25/08 514/561 |
| 2004/0097871 | A1* | 5/2004 | Yerushalmy | A61M 5/14248 604/65 |
| 2005/0039745 | A1* | 2/2005 | Stahmann | A61B 5/0809 128/204.18 |
| 2005/0043652 | A1* | 2/2005 | Lovett | A61B 5/1116 600/595 |
| 2005/0076908 | A1* | 4/2005 | Lee | A61B 5/4809 600/544 |
| 2005/0080463 | A1* | 4/2005 | Stahmann | A61N 1/36003 600/595 |
| 2005/0115561 | A1* | 6/2005 | Stahmann | A61B 5/02055 128/204.23 |
| 2006/0093785 | A1* | 5/2006 | Hickle | A61M 16/0093 428/121 |
| 2006/0183980 | A1* | 8/2006 | Yang | G16H 20/60 128/920 |
| 2007/0150025 | A1* | 6/2007 | Dilorenzo | G16H 50/30 607/45 |
| 2008/0269630 | A1* | 10/2008 | Denison | A61B 5/4094 600/544 |
| 2010/0185183 | A1* | 7/2010 | Alme | A61M 5/14276 604/891.1 |
| 2014/0378808 | A1 | 12/2014 | Lee | |
| 2014/0379273 | A1* | 12/2014 | Petisce | G16H 15/00 702/19 |
| 2015/0011864 | A1* | 1/2015 | Reisberg | A61K 38/28 514/5.9 |
| 2020/0138366 | A1* | 5/2020 | Low | A61B 5/374 |
| 2021/0169417 | A1* | 6/2021 | Burton | A61B 5/4857 |
| 2021/0205559 | A1* | 7/2021 | Raman | A61B 5/4809 |
| 2021/0275043 | A1 | 9/2021 | Ahmad et al. | |

OTHER PUBLICATIONS

Lancel, Marike, et al. "The GABAA receptor antagonist picrotoxin attenuates most sleep changes induced by progesterone." Psychopharmacology 141.2 (1999): 213-219. (Year: 1999).*

Bierwirth, et al., "Prefrontal Theta Oscillations Are Modulated by Estradiol Status During Fear Recall and Extinction Recall," Biol. Psychiatry Cogn. Nuerosci. Neuroimaging, vol. 6, No. 11, 2021, pp. 1071-1080.

Chen, et al., "Theta oscillations synchronize human medial prefrontal cortex and amygdala during fear learning," Sci. Adv., vol. 7, No. 34, 2021, 13 pages.

Milne, et al., "Altered neural dynamics in people who report spontaneous out of body experiences," Cortex, vol. 111, 2019, pp. 87-99.

Sandkuhler and Bhattacharrya, Deconstructing Insight: EEG Correlates of Insightful Problem Solving, PLOS One, vol. 3, No. 1, 2008, 12 pages.

Sheth, et al., "Posterior Beta and anterior gamma oscillations predict cognitive insight," J. Cogn. Neurosci., vol. 21, No. 7, 2009, pp. 1269-1279.

* cited by examiner

300

| | 302 | 304 |
|---|---|---|
| | DOSE | TYPE OF AIRFLOW COMPONENT |
| 306 | 5 MG | CPAP DEVICE |
| 308 | 5 MG | AIR HUMIDIFIER |
| 310 | 5 MG | OXYGEN THERAPY NASAL CANNULA |
| 312 | 5 MG | NON-REBREATHER MASK KIT |
| 314 | 5 MG | ROOM HUMIDIFIER |

| | 316 | 318 |
|---|---|---|
| | DOSE | TIMING |
| 320 | 5 MG | 11 PM TO 4 AM |
| 322 | 10 MG | 4 AM TO 6 AM |

| PRESCRIPTION DATABASE | | | | | | | | |
|---|---|---|---|---|---|---|---|---|
| USERNAME | DATE: 12/17/2020 | | | | | | | |
| TIMING | 10pm | 11pm | 12am | 1am | 2am | 3am | 4am | 5am |
| DOSE | 5 mg | 5mg | 5mg | 5mg | 5mg | 5mg | 5mg | 10mg |
| PHYSIOLOGICAL PARAMETER | Heart Rate: 90 beats per minute, $SpO_2$: 80 | Heart Rate: 90 beats per minute, $SpO_2$: 80 | Heart Rate: 90 beats per minute, $SpO_2$: 80 | Heart Rate: 90 beats per minute, $SpO_2$: 80 | Heart Rate: 90 beats per minute, $SpO_2$: 80 | Heart Rate: 90 beats per minute, $SpO_2$: 80 | Heart Rate: 100 beats per minute, $SpO_2$: 80 | Heart Rate: 100 beats per minute, $SpO_2$: 80 |
| | Increased body movement | Increased body movement | Increased body movement | Increased body movement | Increased body movement | Increased body movement | Increased body movement | Increased body movement |
| | 402 | 404 | 406 | 408 | 410 | 412 | 414 | 416 |

FIG. 4

SYSTEMS AND METHODS TO AUTOMATICALLY ADMINISTER A PSYCHOACTIVE SUBSTANCE TO AN AIRWAY OF A USER BASED ON A DETECTED EVENT OR CONDITION

FIELD OF THE DISCLOSURE

The current disclosure provides systems and methods to automatically administer a psychoactive substance to an airway of a user based on a detected event or condition. The systems and methods provide a variety of benefits for wellness, wellness research and brain-computer interface training.

BACKGROUND OF ASPECTS OF THE DISCLOSURE

Wellness refers to the state of being in good health. Wellness has both physical and mental components that are inter-related. Mental wellness has been described by The American Mental Wellness Association as "a state of well-being in which the individual realizes his or her own abilities, can cope with the normal stresses of life, can work productively and fruitfully, and is able to make a contribution to his or her community."

A variety of factors can contribute to mental wellness. These factors include an ability to navigate stress; an ability to engage in fun, relaxing and/or immersive experiences; and the ability to achieve restful sleep. However numerous people do not consistently achieve these goals. Therefore, individuals would benefit from systems and methods that assist them in achieving mental wellness. Further, research into mental wellness is an on-going endeavor, and systems and methods to support further elucidation of its mechanisms are in need as additional research tools.

Brain-computer interfaces (BCI) are a class of technologies involving a direct communication pathway between an organic brain and a nonorganic, external device that seek to ameliorate, analyze and augment human physiology and psychology. Currently, the direct communication pathway between brain and device is largely restricted to electrical signals native to human electrophysiology, which are used to create reliable and adaptable neurofeedback circuits between brain and device. However, such direct communication pathways are not necessarily restricted to being electrical in nature. In fact, circuits built solely upon electrical signals and native human electrophysiology are running into limits of brain-computer integration, especially on the brain end.

The disclosure made herein is presented to address these and other considerations.

SUMMARY OF THE DISCLOSURE

The current disclosure provides systems and methods to automatically administer a psychoactive substance to an airway of a user based on a detected event or condition. Detected events or conditions can be during sleep or when a user is awake and/or engaged in an activity. Detected events can include BCI stimuli and responses whereby the methods described herein can be used to reify, reinforce and temper the nascent and sometimes fragile direct communication pathways between brain and device.

Exemplary detected events and conditions include, for example, brain waves and brain signal patterns associated with sleep cycles, dream states, drowsiness, meditation, focused relaxation, unfocused relaxation, A-HA experiences, occurrence of learning; involuntary body movement of a user (e.g., during sleep); voluntary body movement of a user (e.g., during an activity); involuntary nonmovement of a user (e.g. paralysis); heart rate meeting a threshold; blood oxygen saturation meeting a threshold; respiration rate meeting a threshold; body temperature meeting a threshold; skin galvanics meeting a threshold; location of a user generally; location of a user in relation to a starting location; location of a user in a virtual space; distance traveled; velocity of movement; event in a virtual reality setting; event during game play; event-related potentials (e.g. N100, P200, P300, etc.); time or interval set by a "pacemaker", ingestion of a beverage or food product; gastric content; air humidity level; ambient sound level; and/or changed light level.

The system includes a detection component and an administration component in communication with the detection component. The detection component is configured to detect selected events or conditions. The selected events or conditions (collectively referred to herein as "triggers") can be pre-set by a system, may be honed through machine-learning or can be selected by a user, researcher, or in certain circumstances, by a treating professional (e.g., a therapist, nurse, or doctor). The administration component is configured to administer a psychoactive substance to the airway, including nasal passages, of a user based on one or more detected triggers. The administration component includes a storage component and a control component. The storage component stores a psychoactive substance to administer in the event a trigger is detected. The control component allows release of the psychoactive substance.

In some instances, the administration component further includes an airway component and an introducing component in fluid communication with the airway component. The airway component is configured to provide an airflow to the respiratory system, including nasal cavity, of the user. The introducing component is configured to introduce the psychoactive substance into the respiratory system. The introducing component is further configured to introduce the psychoactive substance into the respiratory system in, for example, a vaporized form, in droplets, as small particulates and/or in an aerosolized form.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 3 illustrates an exemplary dosing schedule according to implementations of this disclosure.

FIG. 4 illustrates an example database according to implementations of this disclosure.

DETAILED DESCRIPTION

Figure 1:
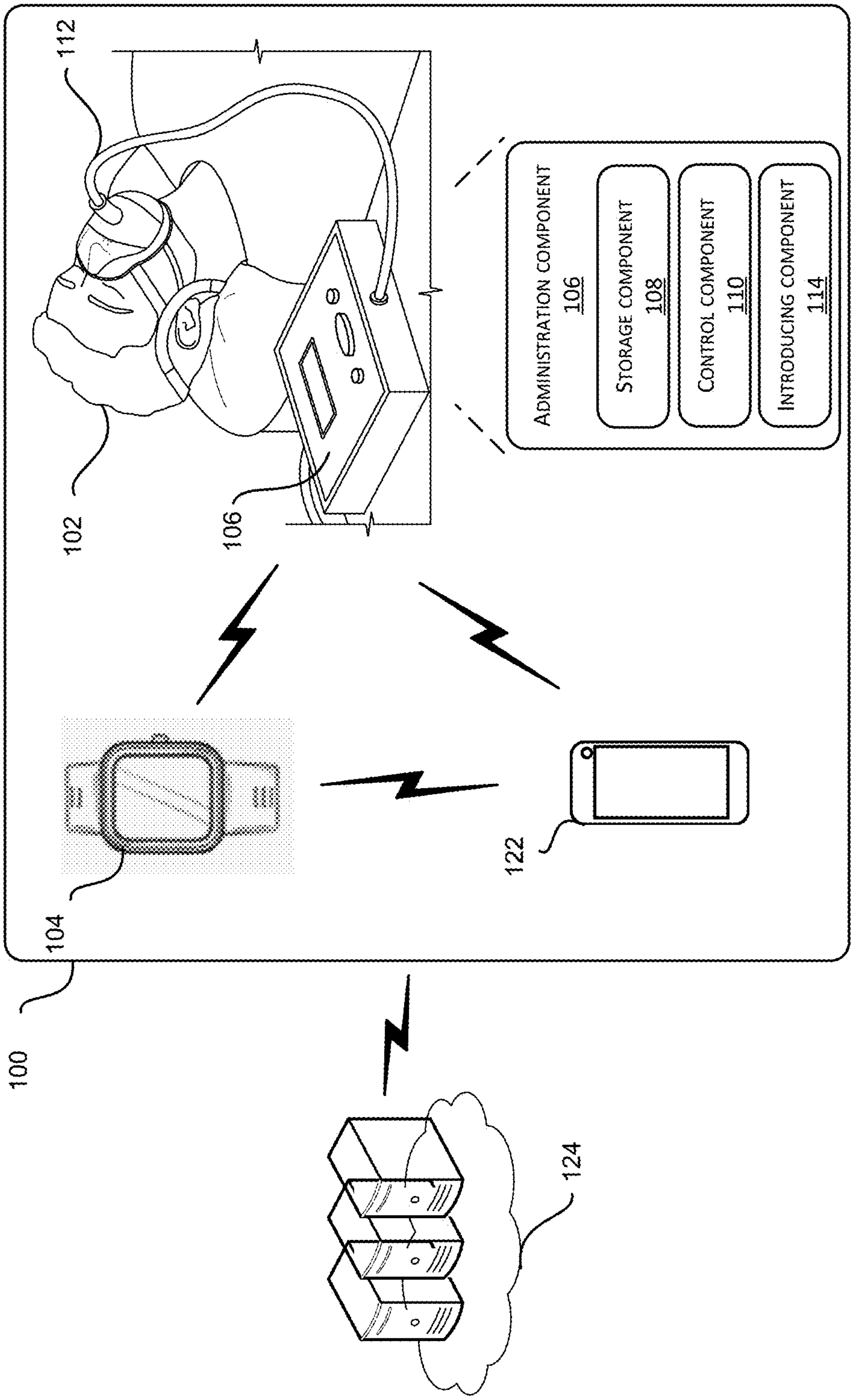
FIG. 1 illustrates an exemplary system for administering a psychoactive substance to a user during sleep based on a detected trigger according to implementations of this disclosure.

Wellness refers to the state of being in good health. Wellness has both physical and mental components that are inter-related. Mental wellness has been described by The American Mental Wellness Association as "a state of well-being in which the individual realizes his or her own abilities, can cope with the normal stresses of life, can work productively and fruitfully, and is able to make a contribution to his or her community."

A variety of factors can contribute to mental wellness. These factors include an ability to navigate stress; an ability to engage in fun, relaxing and/or immersive experiences; and the ability to achieve restful sleep. However numerous people do not consistently achieve these goals. Therefore, individuals would benefit from systems and methods that assist them in achieving mental wellness. Further, research into mental wellness is an on-going endeavor, and systems and methods to support further elucidation of its mechanisms are in need as additional research tools.

Challenges associated with maintaining mental wellness in a purely native organic state are expected to be exacerbated when external devices, such as BCI, are integrated. This may be attributed to signal, circuit and system incoherence generated by internal or external sources of noise. The long-term success of individual BCI will not only depend upon both acceptable and repairable physiological connections but also upon assimilable and correctable psychological connections. A brain's penchant to reject a device is currently a more challenging problem than the reverse. Systems and methods that can overcome such hurdles between brain and device by bulwarking physiological and psychological integration amongst brain and devices are needed.

The current disclosure provides systems and methods to automatically administer a psychoactive substance to an airway of a user based on a detected event or condition. Detected events or conditions can be during sleep or when a user is awake and/or engaged in an activity, real or virtual.

In certain examples, detected events are based on the detection of different brain waves or brain signal patterns. "Brain waves" are distinct from "brain signal patterns" in that a brain wave is defined as a single frequency or narrow frequency band that either occurs at a single time point or repeats with detectable periodicity overtime. Brain signal patterns include at least two signals, which optionally include a brain wave or waves but also include brain events, such as blood flow or oxygen utilization that are not waves per se and are not measured using electroencephalography (EEG) or magnetoencephalography (MEG), that are connected to each other through repeating periodicity or other definable time-based pattern.

The following further elucidates the distinction between brain signals and brain signal patterns, utilizing a hierarchy of complexity, arranged top to bottom, from simpler to more complex measures:

Brain Wave

1. "Brain wave"—a specific frequency or defined frequency range on an electroencephalogram (EEG) at either a single time point or over a short, continuous period (e.g. delta, theta, alpha, beta, gamma)
2. "Brain magnetic wave"—a collection of magnetic field readings begotten by magnetoencephalography (MEG) at either a single time point or over a short, continuous period. Due to less distortion, MEG signals can better pinpoint the location of activity as compared to EEG.

Brain Signal

3. "Functional signals"—Techniques that indirectly measure brain activity by monitoring the blood flow (fMRI), changes in metabolic processes (PET), blood parameters and oxygenation (fNIRS/DOT).

Brain Signal Pattern

4. "Event related potentials/fields (ERP/ERF)"—a specific frequency on an EEG or magnetic flux on MEG that has been amplified and distinguished from irregular noise due to predictable and stereotyped periodicity. It is a collection of the same brain waves or brain magnetic wave signals that repeat overtime (e.g. P100, N100, P200, P300), which constitutes more than a single wave or signal.
5. "EEG+MEG"—Although EEG and MEG essentially measure the same electromagnetic activity of neuronal action the different properties of each contribute different data and thus provide richer spatial and temporal resolution that each alone, i.e. single brain wave. For example, EEG can measure a larger range of brain regions due to the properties of electricity whereas MEG can better determine spatiotemporal resolution of the underlying activity.
6. "Multiple Brain Signals"—overlaying fMRI with PET data, cross-referencing at least two forms of PET tracers, using fMRI or PET with fNIRs, or using all three together constitute a pattern.

Exemplary detected events and conditions include brain signal patterns associated with sleep cycles, dream states, drowsiness, meditation, focused relaxation, unfocused relaxation, A-HA experiences, occurrence of learning; involuntary body movement of a user (e.g., during sleep); voluntary body movement of a user (e.g., during an activity); involuntary nonmovement of a user (e.g. paralysis); heart rate meeting a threshold; blood oxygen saturation meeting a threshold; respiration rate meeting a threshold; body temperature meeting a threshold; skin galvanics meeting a threshold; location of a user generally; location of a user in relation to a starting location; location of a user in a virtual space; distance traveled; velocity of movement; event in a virtual reality setting; event during game play; event-related potentials (e.g. N100, P200, P300, etc.); time or interval set by a "pacemaker", ingestion of a beverage or food product; gastric content; air humidity level; ambient sound level; and/or changed light level.

As examples, particular embodiments detect alpha and theta wave changes indicative of a relaxation phase associated with sleep onset. For example, decreased alpha wave power and increased theta wave power (as compared to when a user is alert (defined as the state of typical waking consciousness dominated by the beta rhythm)) is associated with increased sleepiness. Alpha waves are generally defined as existing in the range of 7 Hz to 12 Hz, as monitored by EEG, and are typically detected above either the occipital lobe (with potential thalamic origin) or frontal central loci. Upon detection (or generation) of these triggers, one or more of the following psychoactive substances can be automatically administered: gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction. Alternatively, these automatically administered substances can be utilized to coax a system into a state exhibiting decreased alpha power and increased theta power.

Particular embodiments detect delta waves indicative of non-rapid eye movement (NREM) or slow wave sleep (SWS), especially deep stage 3 and stage 4 sleep. Delta wave forms are the major electrophysiological signature of stage 4 sleep and are generally defined as occupying the frequency range between 0.1 Hz and 3 Hz. Delta waves decrease with age and can begin to disappear precipitously in the mid- to late-forties and can in some cases become non-existent, along with stage 4 sleep, in septuagenarians. Because delta activity stimulates the release of hormones such as prolactin, growth-hormone releasing hormone (GHRH), and indirectly, growth hormone the deterioration or loss of delta activity can have negative consequences it terms of health, vitality and senescence. Upon detection of this trigger (i.e. sparse or absent delta activity) or to induce such activity as triggered by an external stimuli), one or more of the following psychoactive substances can be automatically administered: *Valeriana officinalis* and compounds thereof, *Humulus lupulus* and compounds thereof, *Rosmarinus officinalis* essential oil and compounds thereof, cannabidiol (CBD), delta-sleep-inducing peptide (DSIP), muramyl dipeptide (MDP), nitrous oxide ($N_2O$), gamma-hydroxybutyrate (GHB) and/or gabapentin.

Particular embodiments detect sleep spindles. Sleep spindles are brief bursts of neural oscillations (9-16 or 11-16 Hz, but commonly 12-14 Hz of 0.5-3 second duration) generated by the interplay of the thalamic reticular nucleus and other thalamic nuclei during NREM sleep (N2 and N3 stages). While spindle waves are generated by the thalamus, they are relayed through thalamocortical oscillations to the cortex. Spindles can be observed in a wide range of thalamic and neocortical structures and are temporally coupled with neocortical slow oscillations (SOs, 0.5-1 Hz) and hippocampal sharp-wave ripples (SWRs, 150-250 Hz) during NREM sleep. It is believed that spindles have functions in both memory consolidation and sensory processing. Research has found that exposure to familiar olfactory cues coincident with sleep spindles not only does not rouse the sleeper or raise the sleep level, but can actually reactivate memory circuits associated with those odor cues. At a high-level, this appears to be a mechanism by which odor-associated, state-dependent learning can be replayed to reinforce sensory processing and promote long-term associative memory consolidation. In addition, there are sex-differences in this effect that appear to be hormonally-mediated, especially by estrogen, such that females are largely found to have an advantage in creating these type of spindle-associated memories. Hormones are critical effectors of often slow-moving chemical circuits. Spindles and SOs might have differential roles in memory consolidation at different sleep stages, or for consolidation of different types of memory traces. In addition, spindles are thought to contribute to a number of neural processes, such as somatosensory development, thalamocortical sensory gating, and synaptic plasticity. Spindles have also been implicated in integrating new memories with existing knowledge. Sleep spindles are a physiological signature of stage-2 NREM sleep and are thought to play a role in isolating the brain from external disturbances during sleep. For example, the quality of the sleep spindle wave form has been correlated with tranquil and uninterrupted sleep. Upon detection of sleep spindles, one or more of the following psychoactive, including aromatic, substances or preparations can be automatically administered: *Valeriana officinalis* and compounds thereof, *Humulus lupulus* and compounds thereof, *Rosmarinus officinalis* essential oil and like as long as the essential oil or odorant has salience to the individual, as well as hormones such as estrogen, progesterone or testosterone depending on the desired effect valence.

Particular embodiments detect K-complexes, which show overlapping frequency ranges with slow waves (0.5-0.8 Hz) and delta activity (1.5-4 Hz) but are observed above different topographical loci of the brain. K-complexes are generally observed in stage 2 NREM sleep, particularly in the first few cycles through the sleep stages, and repeat periodically every 1 to 1.6 minutes. Similar to sleep spindles, which K complexes are sometimes but not always precede, K complexes are believed to function in suppressing cortical arousal to non-threatening stimuli, as judged by the sleeping brain, and to aid memory consolidation. K-complexes are believed to create an electrophysiological "down beat" or "down state" that allows neurons to reboot and find a homeostatic baseline as a countermeasure to the waking state which degrades the signal-to-noise ratio of individual neurons due to the characteristic neuronal activity in the waking state. Sleep apnea is commonly associated with fewer K-complexes than would be expected related to breathing disruptions even though K-complex activity related to auditory stimuli is normal. A trigger such as reduced K-complex occurrence or periodicity can actuate positive pressure breathing optionally associated with substances that increase muscular tone in conjunction with relaxation in the oral cavity or if the goal is to increase sensitivity of the sleeping brain to specific external stimuli, amphetamines can be administered in conjunction with the specific external stimuli as a form of sleep state associative fear-conditioning.

Particular embodiments detect brain signal patterns associated with REM sleep and dream states. Upon detection of this trigger (i.e. trigger B) or upon the detection of another preceding trigger (i.e. trigger A) that reliably predicts trigger B (occurring later in time than trigger A) and then allows accounting for the pharmacokinetic time-course of the substance and route of administration to coordinate pharmacological action with the imminent brain state presaged by trigger B, and termed "electrophysiology-pharmacology programming", one or more of the following psychoactive substances can be automatically administered: galantamine and compounds, especially sesquiterpene lactones, found in *Calea zacatechichi* or *Calea ternifolia* (e.g. Calaxin, Ciliarin, Calein A-F, Calealactones and Caleachromenes).

Particular embodiments include protocols to elicit lucid dreaming. Lucid dreaming is easiest to facilitate during the fourth or fifth sleep cycle and can only occur during REM sleep, which happens at the end of a sleep cycle. Galantamine is understood to facilitate lucid dreaming via inhibiting acetylcholinesterase activity. However, the most reliable currently available protocols for using galantamine to facilitate lucid dreaming involve waking an individual up after about 4.5 hours of sleep, and then having the individual ingest galantamine capsules, remain awake for 0.5 hours and then return to bed where lucid dream induction techniques are practiced while falling back to sleep.

The REM period of the fourth or fifth sleep cycle is roughly around the sixth hour of sleep time so ingesting galantamine at the 4.5 hour mark is a time-based guesstimate of when galantamine should be consumed orally to align with the next or second next REM sleep stage. A 1.5 hour head-start roughly approximates the Tmax of galantamine when consumed orally.

The present disclosure better tailors the timing of galantamine administration by monitoring the progression of the sleep cycle with EEG, and administering galantamine while the sleeper continues to sleep. A protocol is depicted in Table 1.

TABLE 1

Protocol for Galantamine & Lucid Dreaming.

| Pattern | Reference Frame(s) | PK-Intranasal | Trigger | Automatically Administer |
|---|---|---|---|---|
| Periodicity of sleep stages | 1) Previous nights' sleep stage topography (EEG) 2) Preceding sleep stages in existing sleep cycle (EEG) | 1) Tmax = 30-45 min. | 30 min. before sleep cycle 5/6 REM -- Entry into Stage 2 (or Stage 1) sleep depending on individuals patterns and reference frame (EEG) | 1 mg Galantamine via nose-to-brain intranasal device |

This approach also allows more precision based on a shorter pharmacokinetic time-course for galantamine administered via the airways. In this example, intranasal or nose-to-brain administration is preferred.

Particular embodiments detect involuntary body movement of a user (e.g., movement of eye(s), hand(s), arm(s), head, foot/feet, leg(s), and/or torso of the user). Upon detection of these triggers, one or more of the following psychoactive substances can be automatically administered: gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction.

Brain waves exhibiting EEG-monitored frequencies from 12 Hz to 30 Hz, referred to as beta waves, are characteristic of an alert state of consciousness in an individual, though beta activity at even higher frequencies has been observed in different types of mental activities. Upon detection of waning beta wave power in an environment, real or virtual, where an alert waking state is desired certain compounds, such as oxygen, theobromine, caffeine, modafinil, or microdoses of amphetamines can be administered to create and strengthen chemical neurofeedback to train a brain to recognize the electrophysiology underpinning a waning waking state so as to be able to counteract it without the use of the pharmacological intervention in the future. In contrast, the opposite state can be selected for such that waning beta power can be used as a trigger to encourage further waning of beta as a prelude to sleep if the desired outcome is relaxation or sleep. In such a context, this trigger can lead to the automatic administration of gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction.

Particular embodiments detect event related potentials (ERPs) or event related fields (ERFs) that can be measured using EEG and MEG, respectively. Event related potentials differ from standard EEG/wave patterns in that they must be amplified over multiple occurrences to tease the signal away from the background noise since they are often involve a much smaller population of neurons and emit a signal of lesser power that is difficult to distinguish from background noise during a single occurrence. Such ERPs include N100, P200, P300, ELAN, N400, P600/SPS, etc. Upon such triggers a specific pharmacological agent can be automatically administered depending on the current context measured and the future context desired. For example, N100 (a.k.a. N1) is elicited by an unexpected or unpredictable stimulus and often leads to the activation of inhibitory circuits when an individual is focused on something or not if the individual is not focused on a task. Evidence suggest that those suffering from ADHD have lower amplitude N100 signals that seem to impair inhibition of cortical circuits that could prevent distraction. If such an N100 trigger is observed in the context of an environment where the desired state is to keep someone focus or to encourage the individual to focus in similar future states, pharmacological agents that increase focus can be automatically administered such as methylphenidate or amphetamine plus dextroamphetamine. In the opposite context, say for example in the training of a night watchmen, it may be desirous to pharmacologically train an individual to respond to suppress inhibition of circuits that would maintain attention on a current task (e.g. a TV program) and instead encourage exploration of the unexpected and unpredictable stimulus.

Particular embodiments utilize other frequencies of electromagnetic signals both generated by the brain and used to probe that activity. Techniques including functional magnetic resonance imaging (fMRI), functional ultrasound imaging (fUS), positron emission tomography (PET), diffusion tensor imaging (DTI) diffuse optical imaging (DOI), near infrared spectroscopy (NIRS) or event related optical signals (EROS) all allow one to probe the activity of the brain in various ways that can allow pharmalogical feedback circuits to be created by psychoactive substances applied to perturb native circuits to address pathologies or to encourage new behaviors.

Particular embodiments detect A-HA brain signal patterns, which can synonymously be termed "Eureka" brain signal patterns (that can include theta waves, or a spike in anterior cingulate cortical activity see Sandkühler S, Bhattacharya J (2008) Deconstructing Insight: EEG Correlates of Insightful Problem Solving. PLoS ONE 3(1): e1459. https://doi.org/101371/journal.pone.0001459). So-called "Oh Yea" brain signal patterns differ from A-HA (or Eureka) patterns in that an "Oh Yea" pattern results from a clear external origin of insight, e.g. someone shares the answer to a puzzle that an individual has been struggling with or provides a direct hint that leads to the solution. This external origin of insight can be pinned to specific time period, usually within a few seconds and no longer than a few minutes. External sources of insight do not include simply stumbling upon something in the outside world that elicits a solution or something said offhand by an individual that was not intended as a direct cue to solving the problem at hand. A consistent reduction in beta power of 15-25 Hz above the parieto-occipital and centro-temporal regions up to eight seconds before a behavioral response correlate with insight—both internal and external. A-HA brain signal patterns (triggered by internally generated insight) can be discriminated from Oh Yea brain signal patterns (triggered by externally generated insight), by the absence or presence of increased gamma power of 30-70 Hz over the right fronto-central and frontal, respectively (see Sheth B R, Sandkühler S, Bhattacharya J. Posterior Beta and anterior gamma oscillations predict cognitive insight. J Cogn Neurosci. 2009 Jui; 21(7):1269-79. doi: 10.1162/jocn.2009.21069. PMID: 18702591), relative to the average gamma power demonstrated by a particular individual in an awake, problem-solving state. Theta waves are generally 6 Hz to 8 Hz, as monitored by EEG. Upon detection of a lack of such brain signal patterns or an incoherent signal correlate, one or more of the following psychoactive substances can be automatically administered: small, transient doses of the classical (psilocybin, mescaline, LSD) and non-classical (DMT, 5MeO-DMT, salvinorin) psychedelics.

Achieving the A-HA state is often achieved by breaking an especially high gamma rhythm pattern. Gamma is associated with focused attention and large scale brain activity. Gamma waves are characterized as all EEG-monitored brain activity above 30 Hz. Decreasing gamma is akin to stimulating lateral thinking or creativity by decreasing the dominant brain activity pattern(s). Upon detection of this trigger, one or more of the following psychoactive substances can be automatically administered: small, transient doses of the classical (psilocybin, mescaline, LSD) and non-classical (DMT, 5MeO-DMT, salvinorin) psychedelics.

Particular embodiments detect voluntary body movement of a user (e.g., intended movement of eye(s), hand(s), arm(s), head, foot/feet, leg(s), and/or torso of the user)). Upon detection of these triggers, one or more of the following psychoactive substances can be automatically administered: gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction.

Particular embodiments detect heart rate meeting a threshold indicative of an increase. Such embodiments detect activity in the central nucleus of the amydgala and the prefrontal cortex (PFC) to corroborate whether the non-CNS trigger is primarily the result of fear, anxiety and or stress is clarified by the activity present in the amygdala and communication with the PFC to establish fear and anxiety brain patterns. Since the amygdala occupies a non-surface brain region it is not generally amenable to probing using techniques such as EEG/MEG except in the rare case that probes can be implanted inside the brain in contrast to typical EEG/MEG sensor arrays located external to skull or, at least on the surface of the brain. So activity in the amygdala can only generally be assessed using techniques such as fMRI or PET that measure an increased use of resources in the amygdala, which is itself an important signal to be used as part of a brain signal pattern. In contrast, the PFC can be probed using EEG/MEG based techniques which is important since it has been shown that increasing amplitude/power of theta waves between the medial prefrontal cortex (mPFC) and the amygdala is important for the synchronization of learned fear responses. In addition, dorsal mPFC (dmPFC) activity has been shown to precede amygdala activity in time and predict the strengthening or weakening of fear-association. (Chen, Si et al. "Theta oscillations synchronize human medial prefrontal cortex and amygdala during fear learning." Science advances vol. 7,34 eabf4198. 18 Aug. 2021, doi:10.1126/sciadv.abf4198) In addition, it has been shown that heightened fear expression and extinction can be modulated by estradiol demonstrating that observed sex-differences in this area are not mere sex-differences, but are more proximally chemo-signalling differences. (Philipp Bierwirth, Matthias F. J. Sperl, Martin I. Antov, et al. Prefrontal Theta Oscillations Are Modulated by Estradiol Status During Fear Recall and Extinction Recall, Biological Psychiatry: Cognitive Neuroscience and Neuroimaging, Volume 6, Issue 11, 2021, Pages 1071-1080, ISSN 2451-9022, https://doi.org/10.1016/j.bpsc. 2021.02.011.) Upon detection of these triggers, and more importantly the brain patterns that they represent, cannabidiol or benzodiazepines to decrease resting systolic BP and stroke volume can be automatically administered if the desire is to quell or unlearn the emotional state.

Particular embodiments detect blood oxygen saturation, respiration rate, body temperature, and/or skin galvanics reaching a threshold. Upon detection of a threshold trigger indicative of a fear response, tetrahydrocannabinol (THC) can be administered to increase the perception of anxiety whereas oxytocin may be administered to decrease the perception of fear and inculcate a trust response to such triggers.

Particular embodiments detect a user that is predisposed toward experiencing an out of body experience (OBE) or not using EEG and subsequently training individuals to either recognize this state using specific triggers or to enter this predisposed state, respectively. The work of Myles Jones (Milne E, Dunn S, Zhao C, Jones M. Altered neural dynamics in people who report spontaneous out of body experiences. Cortex. 2019 February; 111:87-99. doi: 10.1016/j.cortex.2018.10.019. Epub 2018 Nov. 3. PMID: 30472385, has demonstrated that individuals predisposed toward OBEs show that power of the visual P100 ERP deflection and the consistency of alpha phase locking were reduced. This suggests alterations in timing of processing visual information. If the objective is to train individuals to become more susceptible to OBE, then detection of a normal visual P100 ERP deflection and alpha wave locking could act as a trigger pattern to time the administration for future visual P100 signals since ERPs tend to repeat at regular intervals. In such a scenario, ketamine, *Salvia divinorum* (especially salvinorin A), lysergic acid diethylamide (LSD) and 1-propionyl-lysergic acid diethylamide (1P-LSD) can be administered in the appropriate subthreshold doses. Further fMRI can be used to identify the timing of activation patterns that resemble those found in individuals experiencing OBEs, such as contemporaneous activation of the supramarginal and posterior superior temporal gyri as well as cerebellum activity indicating the perception of movement. The motion of an avatar connected to the identity of a subject can be used as a trigger to induce an experience of OBE in the corporeal individual by automatically administering properly timed infusions of ketamine, *Salvia divinorum* (especially salvinorin A), lysergic acid diethylamide (LSD) and 1-propionyl-lysergic acid diethylamide (1P-LSD).

Particular embodiments include protocols to an OBE, aligned with a virtual experience. Virtual reality is currently limited by using only visual, auditory and somatosensory stimuli to convince a VR participant that their body and soul are experiencing the events that their avatar is experiencing in the virtual world. Methods to integrate olfactory and gustatory stimuli may also be incorporated in the near future.

The present disclosure enables a much deeper range of stimuli—beyond the five sense—to further dissolve the boundary between a non-VR and VR state to aid in the suspension of disbelief. A protocol is depicted in Table 2.

TABLE 2

Protocol for Salvinorin A + Out-of-Body Experiences Aligned with Virtual Reality.

| Pattern | Reference Frame(s) | PK-Inhaled | Trigger | Automatically Administer |
|---|---|---|---|---|
| Constraints of VR narrative timecourse and individual's predilections | 1) Supramarginal and posterior superior temporal gyri activity (fMRI) 2) Cerebellum activity indicating a floating, falling or death sequence (fMRI) | Tmax = 2 min. | 2 min. before OBE or death event in VR. Narrative sequence of VR then subsequently adjusted to align with onset. | 10 mcg/Kg salvinorin A via vaporization followed by inhalation |

Particular embodiments detect ingestion of a beverage or food product. Upon detection of these triggers, a compound to increase dopamine response (e.g., cocaine microdose) and an insulin inducer (e.g., sucrose) can be administered. The insulin inducer can be withheld for non-food pleasure induction.

Particular embodiments detect gastric content and trigger vagus nerve stimulation to activate the parasympathetic nervous system (i.e. rest and digest). Tetrahydrocannabivarin (THCV) can be administered to induce an anorectic effect and mechanical induction of deep-breathing over shallow-breathing.

Particular embodiments detect gastric distress. Upon detection of this trigger, one or more of the following psychoactive substances can be automatically administered: chamomile, ginger, licorice, mint and/or cannabigerol (CBG).

Particular embodiments detect a low air humidity level. Relative humidity is the ratio of water vapor in the air to the amount of vapor that can exist in the air at a given temperature. Warm air can hold more vapor, so while warmer climates tend to feel more humid, cooler air often has higher relative humidity. High humidity can increase wakefulness and reduce the amount of time spent in both slow-wave NREM and REM sleep. Since both of these stages are crucial for the user's overall health, the user may experience additional issues related to bodily recovery and memory consolidation. On the other hand, exposure to excessively low humidity levels can cause dry skin, itchy eyes, and a sore throat. Low humidity has also been linked to respiratory infection. Usually, the comfortable/healthy indoor relative humidity falls between 30% and 50%, and it should not exceed 60%. Other studies suggest 40% to 60% is a better range. As an example, 60% may be an upper comfortable threshold for indoor humidity, while 30% may be a lower comfortable threshold. Outside of these ranges, systems of the current disclosure can automatically administer a psychoactive substance. Upon detection of this trigger, shilajit can be administered to induce bodily protection from low-oxygen, high-elevation, and high UV exposure.

Particular embodiments detect the ambient sound level surrounding a user. Sound is measured in decibels (dB). The following provides decibel ranges associated with certain events and conditions: softest sound that can be heard (0 db); normal breathing (10 db); ticking watch (20 db); soft whisper (30 db); refrigerator hum (40 db); normal conversation, air conditioner (60 db); washing machine, dishwasher (70 db); city traffic (inside the car) (80-85 db); gas-powered lawnmowers and leaf blowers (80-85 db); motorcycle (95 db); approaching subway train, car horn at 16 feet (5 meters), and sporting events (such as hockey playoffs and football games) (100 db); the maximum volume level for personal listening devices; a very loud radio, stereo, or television; and loud entertainment venues (such as nightclubs, bars, and rock concerts) (105-110 db); shouting or barking in the ear (110 db); standing beside or near sirens (120 db); and firecrackers (140-150 db). In implementations, the psychoactive substance may induce greater sensitivity to sound/noise. The systems/methods as described herein may administer certain psychoactive substance upon detection of a trigger such as ambient sound level increasing/decreasing to a certain level. Noise above 70 dB over a prolonged period of time may generate discomfort. Upon detection of this trigger, glutamate can be increased to induce greater sensitivity to sound (e.g., by administering exogenous MSG) or glutamate can be decreased/blocked to cause less sensitivity to sound (by administering, e.g., exogenous GABA, theanine, and/or Withania somnifera (Ashwagandha)).

Particular embodiments detect a changed light level in the user's environment. Poor lighting may cause problems such as insufficient visual contrast and flicker leading to difficulty in recognizing color, text, and graphic details, or to perform tasks with visual demands. On the other hand, excessive light can interfere with the activities of the human central nervous system. Staying in an environment with strong light for an extended time period can make people dizzy, and lead to symptoms such as headache, insomnia, inability to concentrate, and loss of appetite.

Units to characterize light include candles, lumens, footcandles, lux and the International Energy Conservation Code (IECC) 2021 lighting power density (watts per square foot (SF)). When a lux value is provided, the associated footcandle value is $1/10^{th}$ of the value (e.g., 200 lux equals 20 footcandles).

The following provides recommended lux and IECC values of the following types of environments: cafeteria—eating (200-300 lux; 0.40 IECC)); classroom—general (300-500 lux; 0.71 IECC)); conference room (300-500 lux; 0.97 IECC)); corridor—general (50-100 lux; 0.41 IECC)); corridor—hospital (50-100 lux; 0.71 IECC)); dormitory—living quarters (200-300 lux; 0.50 IECC)); exhibit space (museum) (300-500 lux; 0.31 IECC)); gymnasium—exercise/workout (200-300 lux; 0.90 IECC)); gymnasium—sports/games (300-500 lux; 0.85 IECC)); kitchen/food prep (300-750 lux;

1.09 IECC)); laboratory (classroom) (500-750 lux; 1.11 IECC)); laboratory (professional) (750-1200 lux; 1.33 IECC)); library—stacks (200-500 lux; 1.18 IECC)); library—reading/studying (300-500 lux; 0.96 IECC)); loading dock (100-300 lux; 0.88 IECC)); lobby—office/general (200-300 lux; 0.84 IECC)); locker room (100-300 lux; 0.52 IECC)); lounge/breakroom (100-300 lux; 0.59 IECC)); mechanical/electrical room (200-500 lux; 0.43 IECC)); office—open (300-500 lux; 0.61 IECC)); office—private/closed (300-500 lux; 0.74 IECC)); parking—interior (50-100 lux; 0.15 IECC)); restroom/toilet (100-300 lux; 0.63 IECC)); retail sales (200-500 lux; 1.05 IECC)); stairway (50-100 lux; 0.49 IECC)); storage room—general (50-200 lux; 0.38 IECC)); and workshop (300-750 lux; 1.26 IECC)). For example, in response to a simulated night cycle, melatonin and/or adenosine can be administered. In response to a simulated day cycle, caffeine can be administered.

In certain examples, the current disclosure provides protocols for BCI interface stimulated actions. For example, BCI can be used to enable the triggering of automatic action or communication in an individual with a connected device or avatar. Neurofeedback can be used to strengthen the awareness of certain stimuli (e.g. P300) and the acceptance of the BCI-mediated response.

Nevertheless limits exist to long-term viability of the BCI integrated device itself, especially if invasive, and the resulting action that is directed by the BCI can be consciously or unconsciously resisted or weakened by the organic portion of the individual.

The present disclosure enables a chemical domain to be incorporated both in the training of the use of BCI as well as the acceptance of the organic portion of the individual to maintain and strengthen the BCI. Table 3 provides an exemplary protocol.

TABLE 3

Protocol for Oxytocin + Brain-Computer Interface Stimulated Action.

| Pattern | Reference Frame(s) | PK-Intranasal | Trigger | Automatically Administer |
|---|---|---|---|---|
| BCI trained signal such an Event Related Potential, in this case P300 | Preceding P300 states and associated time-marked signals (EEG) | Olfactory bulb concentration > 0 @ 5 min. | 5-10 min. before a predicted P300 signal and subsequent BCI-initiated action. | 1.0 mg of oxytocin via nose-to-brain intranasal device |

Aspects of the current disclosure are now described with additional detail and options as follows: (i) Sensors; (ii) Psychoactive Substances; (iii) Methods of Airway Delivery; (iv) Kits; (v) Methods of Use; (vi) Particular Description of Embodiments Depicted in the Figures; (vii) Exemplary Embodiments; and (viii) Closing Paragraphs. These headings are provided for organizational purposes only and do not limit the scope or interpretation of the disclosure.

(i) SENSORS

As indicated, in certain examples, triggers are detected by one or more sensors that are part of the detection component of disclosed systems. Exemplary sensors include wearable electroencephalography electrodes (EEGs); heart rate monitors; photoplethysmography (PPG) and thermopile sensors; thermometers; pulse oximeters (e.g., infrared pulse oximeters); respiration rate sensors (e.g., radar-based or acoustic respiration rate sensors); sensors that detect electrical conductivity of the skin; telemetric, tube-based, or ingestible sensors to detect gastric conditions (see, e.g., U.S. Pat. No. 8,986,230); location service services (e.g., global positioning system (GPS)); accelerometers; speakers; microphones; recording devices; capacitive humidity sensors; phototransistors; etc.

In certain examples, sensors are worn by a subject, carried by a subject, or are otherwise in a proximity to the subject such that selected triggers can be detected. Exemplary sensors can be part of, for example, a smartwatch, a smart bracelet, smart glasses, smart clothing, smart footwear, a smart armband, a smart belt, smart ring, smart earphone, a chest strap configured to detect a heart rate and/or ECG, a helmet, cap, or headband. As used herein, “smart” refers to the features of having at least one sensor and the ability to transmit data regarding the sensed parameter to an external device.

US 20210275043, entitled “Smart Wristband for Multiparameter Physiological Monitoring” describes a smart wristband worn on the wrist that uses reflective PPG and thermopile sensors contacting the skin of the wrist. With this configuration, the smart wristband acquires 3-channel arterial pulse waveform data, temperature data, and accelerometer data, and utilizes Wi-Fi or Bluetooth protocols to wirelessly stream this data in real-time to a system component running associated software to make data transfer possible. Specialized algorithms, applications, and software running on the system components can analyze the incoming data to evaluate and detect various triggers based on cuffless non-invasive blood pressure (NIBP), $SpO_2$, heart rate, respiration rate, temperature, and user activity. Additionally, the algorithms, applications, and software running on the system components may utilize location services, such as GPS capabilities to detect user location.

Certain examples monitor and analyze brain waves and/or brain signal patterns. Any monitor capable of measuring brain wave activity can be used. Examples of such monitors include EEGs.

US2014/0378808 describes a physiological sensor apparatus including a physiological sensor, a headband, and an eye mask. The sensor senses a signal indicative of a sleep stage of a user. The sleep stage may be a rapid eye movement (REM) stage, a non-rapid eye movement (NREM) stage, or another type of sleep stage used to characterize the state of sleep of the user. The sensor is used to determine the various sleep stages exhibited by the user during a time period of sleep. In one example, the physiological sensor includes a plurality of EEG electrodes configured to sense brain waves when the EEG electrodes are disposed on a forehead of the user.

The headband and eye mask are used to maintain the position of the sensor as it is disposed on the forehead of the user and prevent the electrodes from being displaced during the period of time. The headband is attached to the sensor and is adjustable to fit securely around a forehead of the user. The headband has a first end that attaches to a first clasp located at a first end of the sensor, and the headband has a second end that attaches to a second clasp located at a second end of the sensor. A diameter of the headband is adjustable by the user to secure the sensor to the forehead of the user. The diameter can be adjusted by adjusting, for example, a Velcro portion located at each end of the headband.

The eye mask has a first eye patch portion and a second eye patch portion. The first eye patch portion forms a first lateral edge and a first inner edge. A first attachment mechanism attaches the first lateral edge to the first end of the headband. The second eye patch portion forms a second lateral edge and a second inner edge. A second attachment mechanism attaches the second lateral edge to the second end of the headband. If the headband did not include the attached eye mask, then the sensor would shift away from the forehead due to movements that a typical user undergoes during sleep.

The first and second inner edges of the eye mask extend along a first axis and are adjacent to each other. The sensor extends from the first end of the headband to the second end of the headband along a second axis. The second axis is perpendicular to the first axis. As a result of this configuration, the eye mask is disposed over eyes of the user when the sensor is disposed on the forehead of the user.

A nasal edge is formed by the first eye patch portion and the second eye patch portion. The nasal edge is adapted to be disposed on a nose of the user when the sensor is disposed on a forehead of the user. The first axis bisects the nasal edge. The nasal edge provides additional support to secure the sensor to the forehead during sleep and to prevent the sensor from being displaced. In another embodiment, no nasal edge is present, and the eye mask forms a convex shape. The sensor accurately determines the sleep stages of the user over a period of sleep of the user because the adjustable headband and eye mask prevent the electrodes from being displaced from the forehead of the user during the period of sleep.

In certain examples, sensors are incorporated into a virtual reality (VR) system, such as the Meta (formerly Oculus) Quest 2 or the HTC Vive Pro 2 Headset (for visual information), in combination with haptic suits, such as a TeslaSuit or Rapture Vest, and integrated with VR programming that can create input for such sensory components of the VR system. Additional examples of virtual/augmented reality systems include (Meta) Oculus™ Rift; (Meta) Oculus™ Go; (Meta) Oculus Quest™; Samsung Gear VR; Samsung HDM Odyssey Windows Mixed Reality; HTC Vive™/HTC Vive™ Pro; Vive™ Cosmos Series; HP Reverb™ G2; Playstation™ VR; Nintendo Labo™ VR Kit; Google Daydream View™; Google Cardboard™; Microsoft HoloLens™; Acer™ Windows Mixed Reality; ANTVR; ASUS™ Windows Mixed Reality; Dell Visor™; Galaxy Vision™; GameFace™; HP™ Windows Mixed Reality; Lenovo Explorer™ Windows Mixed Reality; StarVR™; Valve Index™; Varjo™ VR-3; and Vrvana Totem™.

(ii) PSYCHOACTIVE SUBSTANCES

As used herein, psychoactive substances include: (1) any constituent extracted or derived from a plant, fungi or animal belonging to the genuses: *Acacia, Alchornea, Amanita, Amsonia, Anadenanthera, Apocynum, Areca, Argyreia, Artemisia, Arundo, Aspidosperma, Banisteriopsis, Burkea, Calea, Calligonum, Calycanthus, Cannabis, Catha, Carex, Claviceps, Copelandia, Datura, Delosperma, Desfontainia, Desmanthus, Desmodium, Dictyoloma, Diplopterys, Dutaillyea, Echinopsis, Elaeagnus, Erigonum, Erythroxylum, Festuca, Glycyrrhiza, Guiera, Gymnacranthera, Hammada, Heimia, Horsfieldia, Humulus, Ilex, Ipomoea, Iryanthera, Leonotis, Leptactinia, Lespedeza, Limonia, Lolium, Lophophora, Matricaria, Meconopsis, Melicope, Melissa, Mentha, Mimosa, Mitragyna, Mucuna, Nectandra, Newbouldia, Nicotiana, Nymphaea, Opuntia, Osteophloem, Panaeolus, Pandanus, Papaver, Passiflora, Pauridiantha, Peganum, Petalostylis, Phalaris, Phyllodium, Phyllomedusa, Picrasma, Pilocarpus, Plectocomiopsis, Prosopis, Psilocybe, Psychotria, Punica, Rhinella, Rivea, Rosmarinus, Salvia, Shepherdia, Simira, Strychnos, Tabernaemontana, Tabernanthe, Testulea, Tetradium, Trachelospermum, Tribulus, Uncaria, Urtica, Valeriana, Vepris, Vestia, Vinca, Virola, Voacanga, Withania, Zanthoxylum, Zingiber* and *Zygophyllum*; (2) any Compounds in the following chemical classes: arylcyclohexylamines, beta-carbolines, cathinones, ergolines, indole alkaloids, lysergamides, methylxanthine alkaloids, muscimol (and precursors), phenethylamines, salvinorins, tryptamines, *Phyllomedusa* peptides, and generally any compound or class of compounds categorized as "hallucinogenic substance" in schedules 1-5 of the United States Controlled Substance Act or analogues thereof; (3) any Compounds or Formulations that exhibit central nervous system (CNS) activity at adenosinergic, adrenergic, cannabinergic, dopaminergic, GABA, NMDA, norepinephrine, and serotoninergic (e.g. 5-$HT_{2A}$ and 5-$HT_{1A}$) receptors. (see, for example, Shulgin & Shulgin (2007). *Pihkal: A chemical love story*. Berkeley, Calif.: Transform Press; Shulgin & Shulgin (2017). *Tihkal: The continuation*; and Controlled Substances Act of 1970. 21 U.S.C. § 812 (2019); and (4) hormones with chemical signaling effects in the brain. Such psychoactive hormones can be used to entrain neuronal activity. Compounds not falling within one of these classes or groups is not a psychoactive substance within the current disclosure.

Constituents extracted or derived from cannabis include cannabinoids, terpenoids and flavonoids as well as synthetic, semisynthetic or highly purified versions of any such constituent.

In particular embodiments, the psychoactive substance is from a plant in the Cannabaceae family, for example, from a cannabis plant including *Cannabis sativa, Cannabis indica*, and/or *Cannabis ruderalis*.

There are hundreds of strains of *Cannabis sativa* including: Amnesia Haze which is a sativa strain that features up to 25 percent THC with long-lasting body-relaxing and clear-headed effects that are beneficial for dealing with mood problems and tension; Sour Diesel offers 19 percent THC and provides users with an invigorating, yet dreamy cerebral effect; Strawberry Cough has a pungent strawberry scent and tendency to make the consumer cough and contains 24 to 26 percent THC; Jack Herer features between 17 and 18 percent THC and causes users to feel an overwhelming feeling of bliss, giving them a clear head that is ready to tackle a creative project; Tangie or Tangerine Dream is 17 percent THC and provides users with a perfect mix of euphoria and relaxation; Super Lemon Haze is an energizing sativa strain that is 18 percent THC which gives users a jolt of energy after use; and Maui Wowie features sweet pineapple flavors and 18 percent THC giving users a motivated, creative feeling.

As used herein, the term "cannabinoid" is generally understood to include any chemical compound that acts upon a cannabinoid receptor. For instance, cannabinoids may include endocannabinoids (i.e., produced naturally by humans and animals), phytocannabinoids (i.e., found in cannabis and some other plants), and artificial cannabinoids (i.e., manufactured and not naturally occurring).

Examples of cannabinoids include cannabidiol (CBD), cannabigerolic acid (CBGA), cannabigerol (CBG), cannabigerol monomethylether (CBGM), cannabigerovarin (CBGV), cannabichromene (CBC), cannabichromevarin (CBCV), cannabidiol monomethylether (CBDM), cannabidiol-C4 (CBD-C4), cannabidivarin (CBDV), cannabidiorcol (CBD-C1), Δ-9-tetrahydrocannabinol (A9-THC), Δ-9- tetrahydrocannabinolic acid A (THCA-A), Δ-9-tetrahydrocannabionolic acid B (THCA-B), Δ-9-tetrahydrocannabinolic acid-C4 (THCA-C4), Δ-9-tetrahydrocannabinol-C4, Δ-9-tetrahydrocannabivarin (THCV), Δ-9-tetrahydrocannabiorcol (THC-C1), Δ-7-cis-iso tetrahydrocannabivarin, Δ-8-tetrahydrocannabinol (Dd-THC), cannabicyclol (CBL), cannabicyclovarin (CBLV), cannabielsoin (CBE), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9hydroxy-Δ-6a-tetrahydrocannabinol, 8,9-dihydroxy-Δ-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-Δ-6a-tetrahydrocannabionol (OTHC), Δ-9-cis-tetrahydrocannabinol (cis-THC), 3,4,5,6-tetrahydro-7-hydroxy-α-α-2-trimethyl-9-n-propyl-2, 6-methano-2H-1-benzoxocin-5-methanol (OH-iso-HHCV), cannabiripsol (CBR), trihydroxy-Δ-9-tetrahydrocannabinol (triOH-THC), cannabinol propyl variant (CBNV), cannabidiolic acid (CBDA), cannabitriol (CBO), and tetrahydrocannabivarinic acid (THCVA) and derivatives thereof. Further examples of cannabinoids are discussed in PCT Patent Application Pub. No. WO2017/190249 and U.S. Patent Application Pub. No. US2014/0271940.

The term "derivative" in chemistry refers to a compound that is obtained from a similar compound or a precursor compound by a chemical reaction.

Examples of cannabinoids that can be synthetically produced include: naphthoylindoles, naphthylmethylindoles, naphthoylpyrroles, naphthylmethylindenes, phenylacetylindoles, cyclohexylphenols, tetramethylcyclopropylindoles, adamantoylindoles, indazole carboxamides, and quinolinyl esters. Derivatives of natural cannabinoids can include metabolites of cannabinoids which are disclosed in WO 2015/198078. For example, the metabolite of CBD includes 7-OH-CBD and the metabolite of CBDV includes 7-OH-CBDV. In particular embodiments, examples of cannabinoids include 3-carbamoyl-2-pyridone, and its derivatives and/or analogs disclosed in US 2008/0103139; pyrimidine derivatives and/or analogs disclosed in US 2006/0293354; carenadiol and its derivatives and/or analogs thereof disclosed in U.S. Pat. No. 4,758,597; cannabinoid carboxylic acids and their derivatives and/or analogs disclosed in WO 2013/045115; pyrido[3,2-E][1,2,4]triazolo[4,3-C]pyrimidine and its derivatives and/or analogs disclosed in WO 2008/118414; tetrahydro-pyrazolo[3,4-C] pyridine and its derivatives and/or analogs disclosed in WO 2007/112399; bicyclo[3.1.1]heptan-2-one cannabinoid and its derivatives and/or analogs disclosed in WO 2006/043260; resorcinol and its derivatives and/or analogs disclosed in WO 2005/0123051; dexanabinol compounds and their derivatives and/or analogs disclosed in WO 2004/050011; cannabimimetic lipid amide compounds and their derivatives and/or analogs disclosed in WO 2000/032200; nabilone and its derivatives and/or analogs disclosed in US 2010/0168066; 2-oxoquinolone compounds and their derivatives and/or analogs disclosed in US 2003/0191069; and 3,4-diaryl-4,5-dihydro-(h)-pyrazole-1-carboxamide and its derivatives and/or analogs disclosed in US 2011/0137040.

In particular embodiments, 3-carbamoyl-2-pyridone and its derivatives and/or analogs include methyl 3-methyl-2-{[2-oxo-1-(2-oxo-ethyl)-1,2,5,6,7,8,9,10-octahydro-cycloocta[b]pyridine-3-carbonyl]-amino}-butyrate; dimethyl 2-[(1-cyclohexylmethyl-5,6-dimethyl-2-oxo-1,2-dihydro-pyridine-3-carbonyl)-amino]-succinate; and methyl 2-{[1-(3-methoxycarbonyamino-propyl)-2-oxo-1,2,5,6,7,8,9,10-octahydro-cycloocta[b]pyridine-3-carbonyl]-amino}-2-methyl-propionate.

In particular embodiments, pyrimidine derivatives and/or analogs include a compound having Formula (I) (2-((2,4-dichlorophenyl)amino)-N-((tetrahydro-2H-pyran-4-yl) methyl)-4-(trifluoromethyl)pyrimidine-5-carboxamide), Formula (I)

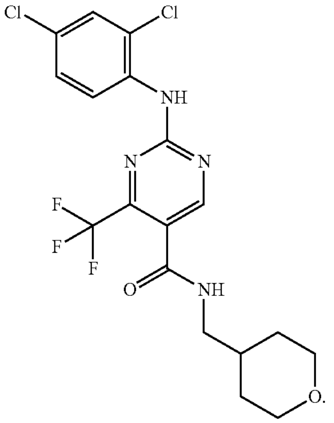

Other pyrimidine derivatives and/or analogs include 2-(3-Chlorophenylamino)-4-trifluoromethylpyrimidine-5-carboxylic acid cyclohexylmethyl-amide; 2-Phenylamino-4-trifluoromethylpyrimidine-5-carboxylic acid cyclohexylmethyl-amide; 1-[2-(2,3-Dichlorophenylamino)-4-trifluoromethylpyrimidin-5-yl]-1-morphol-in-4-yl-methanone; 1-[2-(2,4-Dichlorophenylamino)-4-trifluoromethylpyrimidin-5-yl]-1-morphol-in-4-yl-methanone; and 2-(3-Chlorophenylamino)-4-trifluoromethylpyrimidin-5-carboxylic acid cyclopentylamide.

In particular embodiments, carenadiol and its derivatives and/or analogs include compounds having Formula (II), Formula (II)

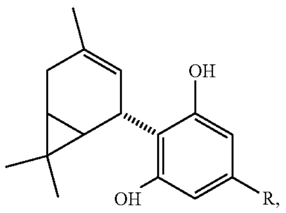

wherein R is a lower alkyl having 1 to 9 carbon atoms including isomeric forms such as i-butyl, n-butyl, and t-butyl. In particular embodiments, R is $C_5H_{11}$ or 1,1-dimethylheptyl.

In particular embodiments, cannabinoid carboxylic acids and their derivatives and/or analogs include compounds having Formula (III), (IV), (V), or (VI), Formula (III)

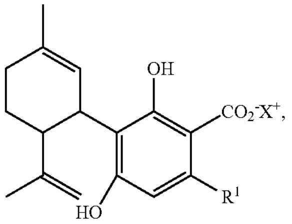

Formula (IV)

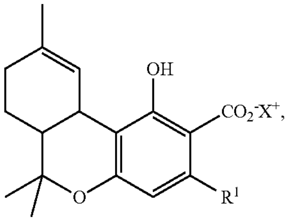

Formula (V)

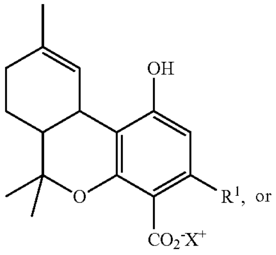

Formula (VI)

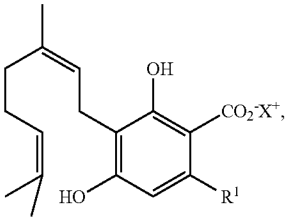

wherein:

- $R^1$ is a straight-chain, branched or cyclic hydrocarbon residue with one C atom to 12 C atoms; and
- $X^+$ is $NH_4^+$, mono-, di- or trivalent metal ions; or primary, secondary, tertiary or quaternary organic ammonium ions with up to 48 C atoms, which may bear still further functional groups.

Examples of multivalent ammonium ions include N,N-dicyclo-hexylamine-$H^+$ and N,N-dicyclohexyl-N-ethylamine-$H^+$. $X^+$ can also be the hydrogen cation of a physiologically active substance with at least one basic nitrogen atom, such as for example morphine, methadone (or an enantiomer thereof) or hydromorphone.

In particular embodiments, pyrido[3,2-E][1,2,4]triazolo[4,3-C]pyrimidine and its derivatives and/or analogs include 5-tert-butyl-8-(2-chlorophenyl)-9-(4-chlorophenyl)pyrido[3,2-e][1,2,4]triazolo[4,3-c]pyrimidin-3(2H)-one; 8-(4-bromo-2-chlorophenyl)-5-tert-butyl-9-(4-chlorophenyl)pyrido[3,2-e][1,2,4]triazolo[4,3-c]pyrimidin-3(2H)-one; 5-fert-butyl-9-(4-chlorophenyl)-8-(2-methylphenyl)pyrido[3,2-e][1,2,4]triazolo[4,3-c]pyrimidin-3(2H)-one; 9-(4-bromophenyl)-5-tert-butyl-8-(2-chlorophenyl)pyrido[3,2-e][1,2,4]triazolo[4,3-c]pyrimidin-3(2H)-one; and 5-tert-butyl-8-(2-chlorophenyl)-9-(4-chlorophenyl)pyrido[3,2-e][1,2,4]triazolo[4,3-c]pyrimidine.

In particular embodiments, tetrahydro-pyrazolo[3,4-C]pyridine and its analogs and/or derivatives include compounds having Formula (VII), (VIII), (IX), (X), or (XI), Formula (VII)

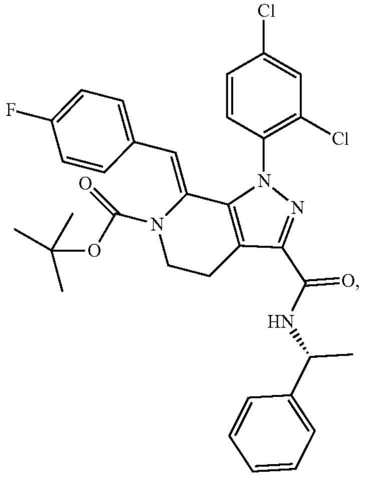

Formula (VIII)

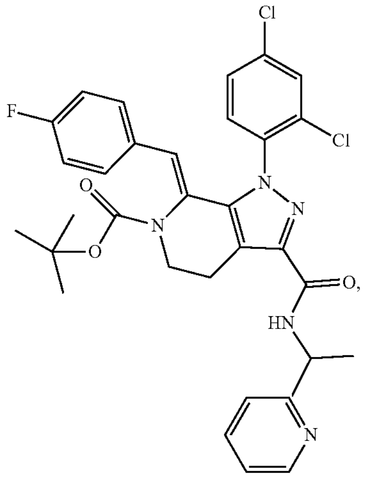

Formula (IX)

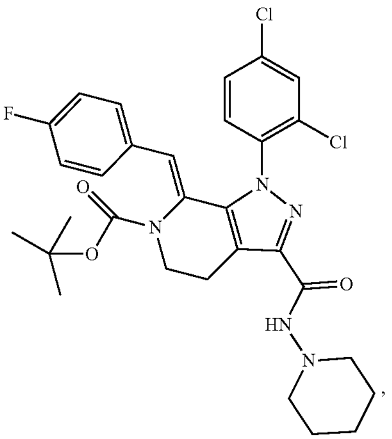

-continued

Formula (X)

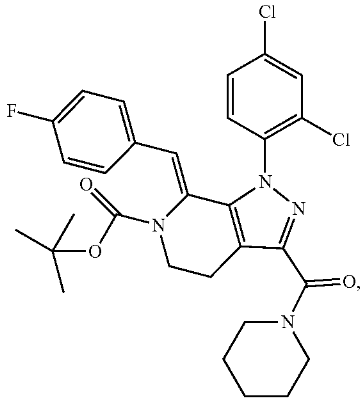

O, or

Formula (XI)

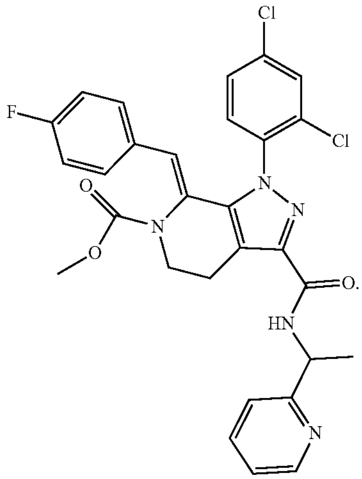

O.

In particular embodiments, bicyclo[3.1.1]heptan-2-one cannabinoids and their derivatives and/or analogs include compounds having Formula (XII), Formula (XII)

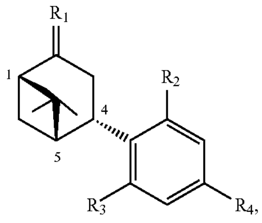

having a specific stereochemistry wherein C-4 is S, the protons at C-1 and C-5 are cis in relation to one another and the protons at C-4 and C-5 are trans; and wherein:

$R_1$ is (a) O or S; (b) $C(R')_2$ wherein R' at each occurrence is independently selected from the group consisting of hydrogen, cyano, —OR", —$N(R")_2$, a saturated or unsaturated, linear or branched $C_1$-$C_6$ alkyl, $C_1$-$C_6$ alkyl-OR" or $C_1$-$C_6$alkyl-$N(R")_2$ wherein at each occurrence R" is independently selected from the group consisting of hydrogen, C(O)R'", C(O)$N(R'")_2$, C(S) R'", saturated or unsaturated, linear or branched $C_1$-$C_6$ alkyl, $C_1$-$C_6$ alkyl-OR'", and $C_1$-$C_6$ alkyl-$N(R'")_2$, wherein at each occurrence R'" is independently selected from the group consisting of hydrogen or saturated or unsaturated, linear, branched or cyclic $C_1$-$C_{12}$alkyl; or (c) NR" or N—OR" wherein R" is as previously defined;

$R_2$ and $R_3$ are each independently (a) —R", —OR", —$N(R")_2$, —SR", —S(O)(O)NR", wherein at each occurrence R" is as previously defined; (b) —S(O)$R^b$, —S(O)(O)$R^b$ wherein $R^b$ is selected from the group consisting of hydrogen, saturated or unsaturated, linear or branched $C_1$-$C_6$alkyl, $C_1$-$C_6$alkyl-OR", and $C_1$-$C_6$alkyl-$N(R")_2$, wherein R" is as previously defined; or (c) —OC(O)OH, —OS(O)(O)$OR^e$, —OP (O)$(OR^e)_2$, —$OR^d$ or —OC(O)—$R^d$ chain terminated by —C(O)OH, —S(O)(O)$OR^e$, or —P(O)$(OR^e)_2$, wherein $R^d$ is a saturated or unsaturated, linear or branched $C_1$-$C_6$ alkyl and Re is at each occurrence selected from the group consisting of hydrogen and $R^d$ as previously defined; and $R_4$ is (a) R wherein R is selected from the group consisting of hydrogen, halogen, OR'", OC(O)R'", C(O)OR'", C(O)R'", OC(O)OR'", CN, $N(R'")_2$, NC(O)R'", NC(O) OR'", C(O)$N(R'")_2$, NC(O)$N(R'")_2$, and SR'", wherein at each occurrence R'" is as previously defined; (b) a saturated or unsaturated, linear, branched or cyclic $C_1$-$C_{12}$ alkyl-R wherein R is as previously defined; (c) an aromatic ring which can be further substituted at any position by R wherein R is as previously defined; or (d) a saturated or unsaturated, linear, branched or cyclic $C_1$-$C_{12}$ alkyl optionally terminated by an aromatic ring which can be further substituted as defined in (c).

In particular embodiments, resorcinol and its derivatives and/or analogs include compounds having Formula (XIII), Formula (XIII)

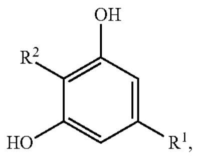

wherein:

$R^1$ is (a) straight or branched alkyl chain of 7 to 12 carbon atoms; (b) —O—$R^3$, where $R^3$ is a straight or branched alkyl chain of 5 to 9 carbon atoms, optionally substituted by one phenyl group; or (c) —$(CH_2)_n$—O—$R^4$, where n is an integer from 1 to 7, and $R^4$ is a straight alkyl chain of 1 to 5 carbon atoms; and $R^2$ is a non-cyclic terpenoid including from 10 to 30 carbon atoms.

In particular embodiments, resorcinol and its derivatives and/or analogs include compounds having Formula (XIII), wherein $R^1$ and $R^2$ are as follows:

$R^1$ is a straight alkyl chain of 5 to 8 carbon atoms, optionally substituted with one methyl group; and $R^2$ is selected from geranyl optionally substituted with one —OH, and farnesyl optionally substituted with one —OH.

In particular embodiments, resorcinol and its derivatives and/or analogs include compounds having Formula (XIII), wherein:

$R^1$ is (a) straight or branched alkyl chain of 7 to 12 carbon atoms; (b) —O—$R^3$, where $R^3$ is a straight or branched alkyl chain of 5 to 9 carbon atoms, optionally substituted by one phenyl group; or (c) —$(CH_2)_n$—O—$R^4$, where n is an integer from 1 to 7, and $R^4$ is a straight alkyl chain of 1 to 5 carbon atoms; and $R^2$ is a non-cyclic terpenoid including from 10 to 30 carbon atoms; with the proviso that when $R^1$ is isononyl, $R^2$ is not geranyl.

In particular embodiments, resorcinol and its derivatives and/or analogs include compounds having Formula (XIII), wherein $R^1$ is (a) a straight or branched alkyl of 7 to 12 carbon atoms; (b) a group —O—$R^3$, where $R^3$ is a straight or branched alkyl of 5 to 9 carbon atoms, or a straight or branched alkyl substituted at the terminal carbon atom by a phenyl group; or (c) a group —$(CH_2)_n$—O-alkyl, where n is an integer from 1 to 7 and the alkyl group contains 1 to 5 carbon atoms.

In particular embodiments, resorcinol and its derivatives and/or analogs include compounds of Formula (XIII), wherein $R^2$ is a non-cyclic terpenoid carbon chain such as geranyl, farnesyl, and related non-cyclic terpenes and their isomers as well as other non-cyclic paraffinic or olefinic carbon chains.

In particular embodiments, resorcinol and its derivatives and/or analogs include compounds of Formula (XIII), wherein $R^1$ is dimethylheptyl and $R^2$ is geranyl.

In particular embodiments, dexanabinol compounds and their derivatives and/or analogs include high enantiomeric purity compounds having Formula (XIV), Formula (XIV)

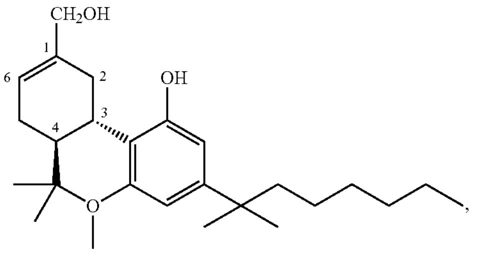

and having the (3S, 4S) configuration and being in enantiomeric excess of at least 99.90% over the (3R,4R) enantiomer.

In particular embodiments, cannabimimetic lipid amide compounds and their derivatives and/or analogs include compounds having Formula (XV), Formula (XV)

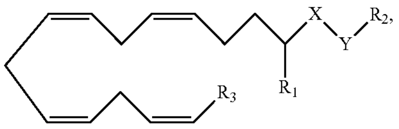

wherein:

X is one of the group consisting of C═O and NH, and Y is the other of that group. Expressed another way, X may be C═O and Y may be NH, or Y may be C═O and X may be NH, but both X and Y may not be the same group.

$R_1$ is H or an alkyl group. In particular embodiments, $R_1$ is H, $CH_3$, or $(CH_3)_2$;

$R_2$ is an alkyl, a substituted alkyl, an alkenyl or an alkynyl group. In particular embodiments, $R_2$ is CH(R) $CH_2Z$, $CH_2CH(R)Z$, or $CH(R)(CH_2)nCH_2Z$; R being H, CH, $CH_3$, CHCH, $CH_2CF_3$, or $(CH_3)_2$; Z being H, halogen, $N_3$, NCS, or OH; and n being selected from the group consisting of 0, 1 and 2.

$R_3$ is an alkyl, a substituted alkyl, an aryl, an alkylaryl, an O-alkyl, an O-alkylaryl, a cyclic and a heterocyclic group. O-alkyl and O-alkylaryl refer to groups in which an oxygen atom is interposed between carbon atoms on the anandamide portion and substituent group. Examples of such $R_3$ groups include cyclohexyl, cyclopentyl, alkylcyclohexyl, alkylcyclopentyl, piperidinyl, morpholinyi and pyridinyl. In particular embodiments, $R_3$ is n-$C_5H_{10}Z'$, n-$C_6H_{12}Z'$, n-$C_7H_{14}Z'$, or 1', 1'-C $(CH_3)_2(CH_2)_5$ $CH_2Z'$; Z' being H, halogens, CN, $N_3$, NCS, or OH.

In particular embodiments, cannabimimetic lipid amide compounds and their derivatives and/or analogs include compounds having Formula (XVI), Formula (XVI)

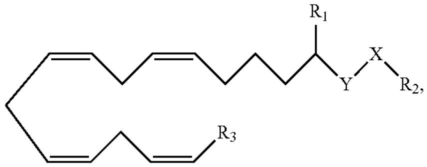

wherein:

Y is one of the group consisting of C═O and NH and X is the other of that group.

$R_1$ is H or an alkyl group. In particular embodiments, $R_1$ is H, $CH_3$, or $(CH_3)_2$.

$R_2$ is an alkyl, a substituted alkyl, an alkenyl, an alkynyl, an O-alkyl, a cyclic, a polycyclic, or a heterocyclic group. In particular embodiments, $R_2$ is

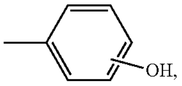 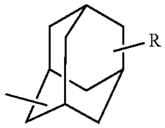, 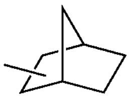,

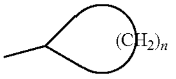 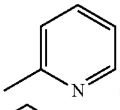, 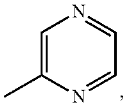,

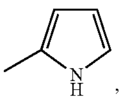, 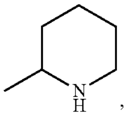, 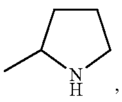, or

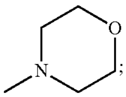

CH═$CH_2$, CH═$C(CH_3)_2$, C═CH, $CH_2OCH_3$, CH(R)$(CH_2)nCH_2Z$, or $CH_2CH(R)(CH_2)nZ$; R being H, $CH_3$ or $(CH_3)_2$; Z being H, halogens, $N_3$, NCS, OH, or OAc; and n 0, 1, or 2; and $R_3$ is an alkyl, a substituted alkyl, an aryl, an alkylaryl, an O-alkyl, an O-alkylaryl, a cyclic, or a heterocyclic group. In particular embodiments $R_3$ includes cyclohexyl, cyclopentyl, alkylcyclohexyl, alkylcyclopentyl, piperidinyl, morpholinyi and pyridinyl. In particular embodiments, $R_3$ is n-$C_5H_{10}Z'$, n-$C_6H_{12}Z'$, n-$C_7H_{14}Z'$, or 1', 1'-$C(CH_3)_2CH_2)_5$ $CH_2Z'$; Z' being H, halogen, CN, $N_3$, NCS, or OH.

In particular embodiments, nabilone and its derivatives and/or analogs include compounds having Formula (XVII):

Formula (XVII)

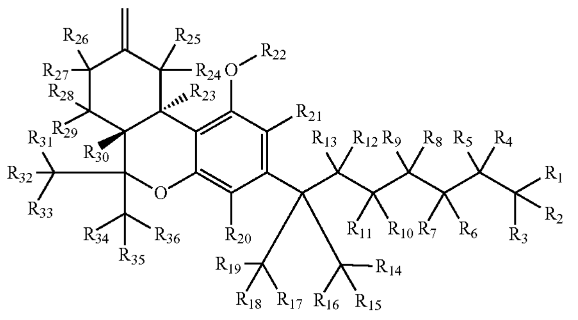

wherein:

$R_1$-$R_{36}$ are independently selected from the group consisting of hydrogen and deuterium. Nabilone derivatives and/or analogs can refer to compounds wherein at least one of $R^1$-$R^{36}$ includes deuterium. The chemical structure of nabilone is:

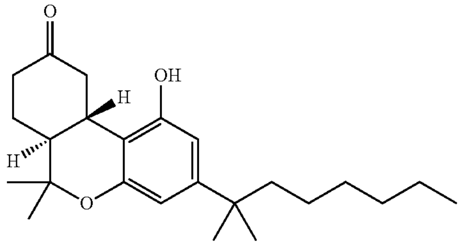 [SMILES: CCCCCCC(C)(C)c1cc(O)c2c(c1)OC(C)(C)[C@H]1CCC(=O)C[C@H]21]

As used herein, a terpene refers to a hydrocarbon or derivative thereof, found as a natural product and biosynthesized by oligomerization of isoprene units (terpenes can also be synthetically produced). A terpene can be acyclic, monocyclic, bicyclic, or multicyclic. Examples include limonene, pulegone, caryophyllene epoxide, bisabalol and the like. As used herein, the term "terpene" includes corresponding terpenoid or sesquiterpenoid compounds. Over 100 different terpenes have been identified in the cannabis plant, and every strain tends toward a unique terpene type and composition. Examples of terpenes include: β-caryophyllene [(lR,4E,9S)-4, 1,l 1-trimethyl-8-methylene-bicyclo (7.2.0)undec-4-ene]; β-caryophyllene oxide; citronellol [3, 7-dimethyl-Δ-octen-l-ol]; α-eudesmol [2-[(2R,4aR)-4a,8-dimethyl-2,3,4,5,6,8a-hexahydro-lH-naphthalen-2-yl]propan-2-ol]; β-eudesmol [2-[(2R,4aR,8aS)-4a-methyl-8-methylidene-l,2,3,4,5,6,7,8a-octahydronaphth-alen-2-yl]propan-2-ol]; gamma-eudesmol [2-[(2R,4aR)-4a, 8-dimethyl-2,3,4, 5,6,7-hexahydro-lH-naphthalen-2-yl]propan-2-ol]; geraniol [(2E)-3,7-dimethylocta-2,6-dien-l-ol]; guaiol [2-[(3S,5R, 8S)-3,8-dimethyl-l,2,3,4,5,6,7,8-octahydroazulen-5-yl]propan-2-ol]; α-humulene [(1E,4E,8E)-2,6,6,9-tetramethylcycloundeca-l,4,8-triene]; β-humulene [(lE,5E)-l,4,4-trimethyl-8-methylidenecycloundeca-l, 5-diene]; gamma-humulene [(1Z,6E)-1,8, 8-trimethyl-5-methy denecy cl oundeca-1,6-diene]; D-limonene [(4R)-l-methyl-4-prop-l-en-2-ylcyclohexene]; L-bmonene [(4S)-l-methyl-4-prop-l-en-2-ylcyclohexene]; (−)-linalool [(3R)-3,7-dimethylocta-1.6-dien-3-ol]; (+)-linalool [(3S)-3,7-dimethylocta-l,6-dien-3-ol]; α-myrcene [2-methyl-Δ-methybdeneocta-1,7-diene]; β-myrcene [7-methyl-3-methylideneocta-l,6-diene]; nerol [(2Z)-3,7-dimethylocta-2,6-dien-l-ol]; cis-nerolidol [(6Z)-3, 7,ll-trimethyldodeca-l,6,10-trien-3-ol]; trans-nerolidol [(6E)-3,7,ll-trimethyldodeca-l,6,10-trien-3-ol]; α-ocimene [(3E)-3,7-dimethylocta-l,3,7-triene]; β-ocimene [(3E)-3,7-dimethylocta-1,3,6-triene]; β-cymene [l-methyl-4-(l-methylethyl)benzene]; α-phellandrene [2-methyl-5-propan-2-yl-cyclohexa-l, 3-diene]; β-phellandrene [3-methybdene-A-propan-2-ylcyclohexene]; cis-phytol [(Z,7R,l lR)-3,7,ll,15-tetramethylhexadec-2-en-l-ol]; trans-phytol [(E,7R,llR)-3,7, ll,15-tetramethylhexadec-2-en-l-ol]; (−)-alpha-pinene [(1S, 5S)-4.6.6-trimethylbicyclo[3.1.1]hept-3-ene]; (−)-α-pinene [(IS,5S)-6,6-dimethyl-4-methylidenebicyclo[3.l.l]heptane]; (+)-α-pinene [(IR,5R)-4,6,6-trimethylbicyclo[3.1. l]hept-3-ene]; (+)-β-pinene [(IR,5R)-6,6-dimethyl-4-methylidenebicyclo[3.1. l]heptane]; (−)-pulegone [(5S)-5-methyl-2-propan-2-yldenecyclohexan-l-one]; (+)-pulegone [(5R)-5-methyl-2-propan-2-ybdenecyclohexan-l-one]; α-terpinene [l-methyl-4-propan-2-ylcyclohexa-l, 3-diene]; Δ-terpinene [5-methyl-2-propan-2-ylcyclohexa-1,3-diene]; γ-terpinene [l-methyl-4-propan-2-ylcyclohexa-4-diene]; α-terpineol [2-(4-methylcyclohex-3-en-l-yl)propan-2-ol]; γ-terpineol [1-methy l-4-propan-2-y lidenecy clohexan-1-ol]; and (+)-valencene [(3R,4aS,5R)-4a,5-dimethyl-3-prop-l-en-2-yl-2, 3,4,5,6,7-hexahydro-lH-naphthalene].

In particular embodiments, wherein tryptamine and its derivatives and/or analogs include compounds having Formula (XVIII):

Formula XVIII

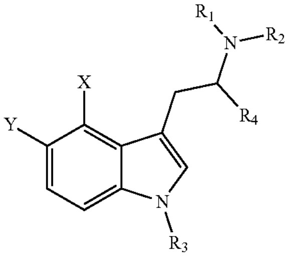

Wherein:

$R_1$, $R_2$, $R_4$ are independently selected from the group consisting of hydrogen, linear alkyl and branched alkyl. $R_3$ is selected from hydrogen or benzyl. X is selected from hydrogen, oxygen (including O— salts), and oxygen ethers. Y is, independent from X, selected from hydrogen, oxygen (including O— salts), and oxygen ethers.

In particular embodiments, wherein phenethylamines, namely phenethylamines of the 2C series and derivatives and/or analogs include compounds having Formula (XIX):

Formula XIX

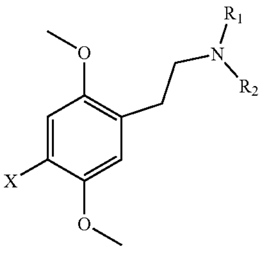

Wherein:

$R_1$ and $R_2$ are independently selected from the group consisting of hydrogen, alkyl, aryl and benzyl. X is selected from hydrogen, alkyl, halide (F, Cl, Br, and I), sulfur or boron.

(iii) METHODS Of AIRWAY DELIVERY

Particular embodiments can use a continuous positive airway pressure (CPAP) machine to automatically administer psychoactive substances to a user based on a detected trigger. CPAP machines include a mask or other device that fits over a user's nose or the user's nose and mouth, straps to position the mask, a tube that connects the mask to the machine's motor, and a motor that blows air into the tube. CPAP machines have historically been used to treat sleep-related breathing disorders, such as sleep apnea. CPAP machines are commercially available. Highly-rated CPAP machines in 2022 include AirMini™ AutoSet™ Travel CPAP Machine; AirMini™ Travel CPAP Machine Bundle with FREE AirFit™ N20 Nasal Mask; AirMini™ Travel CPAP Machine Bundle with FREE AirFit™ P10 Nasal Pillow Mask; AirMini™ Travel CPAP Machine Bundle with FREE AirTouch™ F20 Full Face Mask; AirMini™ Travel CPAP Machine Bundle with FREE AirFit™ F30 Full Face Mask; AirMini™ Travel CPAP Machine Bundle with FREE AirFit™ F20 Full Face Mask; AirSense 10 AutoSet with Heated Humidifier+P10 Nasal Pillow Mask Bundle; AirSense 10 AutoSet with Heated Humidifier+Aifit N30i Nasal Mask Bundle; AirSense 10 AutoSet with Heated Humidifier+P30i Nasal Pillow Mask Bundle; AirSense™ 10 AutoSet™ For Her CPAP Machine with HumidAir™ Heated Humidifier; ComfortPAP Auto 804 CPAP Machine with Therapy Software; DreamStation 2 Auto CPAP Advanced with Humidifier; F&P SleepStyle™ Auto CPAP Machine; GoodKnight 420E Auto CPAP Machine; iCH Auto CPAP Machine with PVA and Built-In Heated Humidifier; Luna Auto CPAP Machine with Integrated H60 Heated Humidifier; Luna II Auto CPAP Machine with Humidifier; Luna II Auto CPAP Machine with Mask Bundle; M Series Auto CPAP Machine with C-Flex; REMstar Auto C-Flex CPAP Machine; ResMed AirSense™ 10 AutoSet™ CPAP Machine with HumidAir™; ResMed S8 AutoSet Vantage™ EPR™ Auto CPAP Machine; Sandman Auto HC CPAP Machine with Built In Heated Humidifier; SleepStyle 254 Auto CPAP Machine with Built In Heated Humidifier; Somnetics Transcend 3 Auto miniCPAP; Transcend 365 Auto CPAP; Zzz-PAP Auto CPAP Machine with Therapy Software; Z2 Auto Travel CPAP Machine; 3B Medical Luna II QX Auto CPAP with Heated Humidifier; and S8 AutoSet™ II CPAP Machine.

Particular embodiments can use a nasal cannula (NC) to administer psychoactive substances to a user. A nasal cannula is a device generally used to deliver supplemental oxygen or increased airflow to a user in need of respiratory help. A nasal cannula includes a tube, where one end of the tube splits into two prongs which are placed in the nostrils of the user and from which a mixture of air and oxygen flows, and the other end of the tube is connected to an oxygen supply such as a portable oxygen generator, or a wall connection in a hospital via a flowmeter. A nasal cannula is generally attached to the user by way of the tube hooking around the user's ears or by an elastic headband. Typical nasal cannulae include curved prong cannula, flared prong cannula, curved and flared prong cannula, and straight prong cannula.

Particular embodiments can use a Venturi mask to administer psychoactive substances to a user. A venturi mask, also known as an air-entrainment mask, is generally used as a medical device to deliver a known oxygen concentration to a user on controlled oxygen therapy. A Venturi mask includes a narrowed aperture with side holes and relies on the Bernoulli effect.

Particular embodiments can use a nebulizer to administer psychoactive substances to a user. A nebulizer is a machine that creates a mist out of liquid medication, allowing for quick and easy absorption of medication into the lungs of the user. A nebulizer includes a base that holds an air compressor, a container for liquid medication, and a tube that connects the air compressor to the container. Typical nebulizers include jet nebulizers, ultrasonic nebulizers, soft mist inhalers and mesh nebulizers.

Particular embodiments can use a non-rebreather mask to administer psychoactive substances to a user. A non-rebreather mask is a device generally used to assist in the delivery of oxygen therapy. A non-rebreather mask includes a reservoir bag to supply 100% oxygen and makes up for the deficit in oxygen supply which occurs during times when a user's Peak inspiratory flow rates (PIFR) is higher than the oxygen flow to the mask from $O_2$ source, a one-way flap valve to prevent expired gas entering the reservoir, and a one-way flap valve to prevent indrawing of room air during inspiration.

Particular embodiments can use an anesthetic facemask to administer psychoactive substances to a user. An anesthesia facemask is a rubber or silicone mask that covers both the mouth and nose of the user. An anesthesia face mask is generally used to deliver $O_2$, $N_2O—O_2$, and/or other inhalation anesthetics before, during, and after an anesthetic procedure. Typical anesthesia face masks include Patil-Syracuse masks and the endoscopy masks.

Particular embodiments can use a humidifier to administer psychoactive substances to a user. A humidifier is a device, primarily an electrical appliance, that increases humidity (moisture). Typical humidifiers include evaporative humidifiers, impeller humidifiers, and ultrasonic humidifiers. An evaporative humidifier includes a reservoir for containing liquid, a wick for absorbing liquid from the reservoir, and a fan for blowing air onto the wick to aid in the evaporation of the liquid. An impeller humidifier includes a rotating disc to fling water at a diffuser, which breaks the water into fine droplets that float into the air. An ultrasonic humidifier uses a ceramic diaphragm vibrating at an ultrasonic frequency to create water droplets that silently exit the humidifier in the form of cool fog.

Particular embodiments can use a ventilator to administer psychoactive substances to a user. A ventilator is a machine that provides mechanical ventilation by moving breathable air into and out of the lungs.

Particular embodiments can use an intranasal delivery device to administer psychoactive substances to a user. A intranasal delivery device can be include atomization devices, such as the MAD Nasal Device™ or nasal spray devices, including unit-dose, bi-dose, and multi-dose variations and such intranasal devices can be optionally used with airflow targeting technology that directs the atomized material or spray plume to various locations of the nasopharynx including the nasal cavity, cribiform plate, olfactory bulb, and olfactory tract. Included in the nasopharynx is the so-called nose-to-brain axis which includes substance traveling along the olfactory and trigeminal nerves into cerebrospinal fluid (CSF) or directly into brain tissues.

(iv) KITS

Kits disclosed herein include at least some of the components needed to practice the systems and methods disclosed herein. In certain examples, the kits include one or more parts of detection components. For example, kits can include sensors to detect a trigger or triggers of interest. For example, a "sleep monitoring" kit could include EEG sensors. An "activity monitoring" kit could include an accelerometer and/or a location detection sensor (e.g., GPS sensor). Kits including aspects of detection components can include one or more of, for example, a smartwatch, a smart bracelet, smart glasses, smart clothing, smart footwear, a smart armband, a smart belt, smart ring, smart earphone, a chest strap configured to detect a heart rate and/or ECG, a helmet, cap, or headband configured to detect brain waveforms/activity, etc.

Additional examples can include one or more of EEGs; heart rate monitors; photoplethysmography (PPG) and thermopile sensors; thermometers; pulse oximeters (e.g., infrared pulse oximeters); respiration rate sensors (e.g., radar-based or acoustic respiration rate sensors); sensors that detect electrical conductivity of the skin; telemetric, tube-based, or ingestible sensors to detect gastric conditions (see, e.g., U.S. Pat. No. 8,986,230); location service services (e.g., global positioning system (GPS)); accelerometers; speakers; microphones; recording devices; capacitive humidity sensors; phototransistors; etc.

Certain examples of kits can include aspects of administration components. For example, kits can include air humidifiers, and/or airway delivery tubes or masks. Kits including administration components can include a CPAP machine (or components thereof), a nasal cannula (or components thereof), a venturi mask (or components thereof), a nebulizer (or components thereof), a non-rebreather mask (or components thereof), an anesthetic facemask (or components thereof), a ventilator (or components thereof), and/or nasal delivery devices (or components thereof).

Particular embodiments include a psychoactive substance disclosed herein or a group of psychoactive substances for administration upon detection of a pre-selected trigger. Exemplary psychoactive substance groupings include gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction; *Valeriana officinalis* and compounds thereof, *Humulus lupulus* and compounds thereof, *Rosmarinus officinalis* essential oil and compounds thereof, and/or cannabidiol (CBD); Galantamine and compounds, especially sesquiterpene lactones, found in *Calea zacatechichi* or *Calea ternifolia* (e.g. Calaxin, Ciliarin, Calein A-F, Calealactones and Caleachromenes); psilocybin, mescaline, LSD, DMT, 5MeO-DMT, and/or salvinorin); cannabidiol; tetrahydrocannabinol (THC); Ketamine and/or *Salvia divinorum* (salvinorin A); cocaine and an insulin inducer (e.g., sucrose); Tetrahydrocannabivarin (THCV); chamomile, ginger, licorice, mint and/or cannabigerol (CBG); Shilajit; MSG, GABA, theanine, and/or Withania somnifera (Ashwagandha)); and melatonin and/or caffeine.

Some kits can include components of a game or a virtual reality (VR) system, such as the Meta (formerly Oculus) Quest 2 or the HTC Vive Pro 2 Headset (for visual information), in combination with haptic suits, such as a TeslaSuit or Rapture Vest, in combination with scent generators, such as Simulreal Olfactory Engine, that releases organoleptic molecules onto taste and smell receptors, and integrated with VR programming that can create input for such sensory components of the VR system.

(v) METHODS Of USE

In particular embodiments, systems and methods disclosed herein can be used in personal and/or research, settings. For example, in certain instances, systems and methods disclosed herein are practiced at home. For example, in preferred instances, systems and methods disclosed herein are practiced in a sleep laboratory. For example, in certain instances, systems and methods disclosed herein are practiced on a long-distance transport vessel. For example, in certain instances, systems and methods disclosed herein could be practiced a group gaming center. For example, in certain instances, systems and methods disclosed herein could be practiced at a neurofeedback or BCI surgical center. For example, in certain instances, systems and methods disclosed herein could be practiced in conjunction with cryogenic life support systems.

In certain examples, systems and methods disclosed herein are practiced in a research setting (e.g., sleep or wellness clinic). Currently, sleep recording for most research or diagnostic purposes is performed in sleep laboratories and is called polysomnography (PSG).

Polysomnography generally involves the acquisition of a number of different signals of a subject. Three of these groups of signals (namely cerebral activity, skeletal muscle tone, and electrooculogram) can be summarized in a hypnogram, which represents the totality of sleep stages (i.e., levels and types of sleep) that occur during a sleep session.

Determining which "stage" of sleep a subject is experiencing during a sleep session is routinely performed in this setting by sleep technologists who manually identify each stage based on standard scoring criteria.

For example, stage 1 is the beginning of a sleep cycle, which is relatively light sleep. During this stage, the brain produces alpha waves. However, during stage 2 sleep, the brain produces rapid, rhythmic brain wave activity known as sleep spindles. In stage 3, which is a transitional stage between light and deep sleep, the brain begins to produce delta waves, which are slow. Then, in stage 4, the brain is in a deep sleep and produces many delta waves (depending on the particular sleep classification system being used, in some cases stage 3 sleep and stage 4 sleep may be grouped together and referred to simply as slow-wave sleep (SWS)). Finally, in stage 5, the brain enters Rapid Eye Movement (REM) sleep, also known as active sleep. This is the stage in which the majority of dreaming will occur. Within the current disclosure, in a sleep lab, psychoactive substances can be automatically administered to the sleep subject based on input from a sleep technologist and/or based on sensed EEG recordings.

In certain examples, systems and methods disclosed herein are practiced at a venue, such as a concert venue. For example, psychoactive substances can be automatically administered based on sound and/or light levels reaching various thresholds.

In certain examples, systems and methods disclosed herein are practiced during an immersive experience, such as while at a movie (e.g., an IMAX movie) or on a ride at an amusement park.

In certain examples, systems and methods disclosed herein are practiced during a virtual experience. Specific examples of events or triggers in a virtual space include running, jumping, floating, flying, swimming, falling, sleeping, dreaming, experiencing an injury, experiencing an adverse event, rehabilitating, eating, copulating, meditating and dying.

In certain examples, systems and methods disclosed herein are practiced during physical or virtual game play. Specific examples of events or triggers in physical game play include running, jumping, swimming, falling, sleeping, dreaming, experiencing an injury, experiencing an adverse event, winning a contest of skill, winning a contest of chance, discovering buried treasure, eating, copulating, or meditating. Specific examples of events or triggers in virtual game play include running, jumping, floating, flying, swimming, falling, sleeping, dreaming, experiencing an injury, experiencing an adverse event, winning a contest of skill, winning a contest of chance, discovering buried treasure, powering-up, eating, copulating, meditating and dying.

In certain examples, systems and methods disclosed herein are practiced during performance of a task, such as a cognitive task.

In certain examples, systems and methods disclosed herein are practiced during a recreational event, such as a festival or a picnic.

In certain examples, systems and methods disclosed herein can be used in therapeutic settings, under the direction of a care provider.

(vi) PARTICULAR DESCRIPTION OF EMBODIMENTS DEPICTED IN THE FIGURES

FIG. 1 illustrates an example system 100 for administering psychoactive substance to a user 102 during sleep based on a detected trigger according to implementations of this disclosure.

Referring to FIG. 1, the system 100 includes a detection component 104 and an administration component 106 in communication with the detection component 104. In some instances, the detection component 104 and the administration component 106 are in wireless communication with each other, for example, through radio broadcast (RF), infrared (IR), microwave, Bluetooth, Wi-Fi, and so on. In some instances, the detection component 104 and the administration component 106 are in wired communication with each other, for example, through hardwired connection, cable, fiber-optic, and so on.

The detection component 104 is configured to detect triggers, for example, selected events or conditions. In some instances, the triggers include occurrence of a pre-set event or a pre-set condition being met. In some instances, the triggers include one or more physiological parameters associated with the user 102 meeting a certain condition, for example, reaching a threshold, and/or falling within a range. The certain condition can be pre-set by a system, or can be selected by a user, researcher, or in certain circumstances, by a professional (e.g., a therapist, nurse, or doctor). In some instances, the one or more physiological parameters associated with the user 102 include a brain signal pattern associated with the user, heart rate associated with the user 102, a blood oxygen saturation associated with the user, and/or an amount of body movement associated with the user. In some instances, the one or more physiological parameters associated with the user 102 further include other physiological parameters that reflect the sleep state of the user. In some instances, the one or more physiological parameters associated with the user 102 further include other physiological parameters that reflect the respiration state associated with the user 102 such as an airway flow rate associated with the user 102, an airway pressure associated with the user 102, and so on. In some instances, the one or more physiological parameters associated with the user 102 further includes a body temperature associated with the user 102, an ECG associated with the user 102, brain waves/activity associated with the user 102, a sound/noise level associated with the user 102, and so on.

The detection component 104 includes one or more sensors configured to sense the one or more physiological parameters associated with the user 102. For example, the one or more sensors can include an EEG, a heart rate sensor, an oxygen saturation sensor, and a body movement sensor (e.g., accelerometer) among other sensor types described elsewhere herein or otherwise known to those of ordinary skill in the art. For example, the detection component 104 includes test probes and/or electrodes affixed to the user 102. In some instances, the one or more sensors may be integrated into the administration component 106. In some instances, the detection component 104 further includes other types of sensors configured to detect physiological parameters associated with the sleep state of the user 102 such as a sensor configured to detect when the user 102 falls asleep, a sensor configured to detect when the user 102 wakes up, a sensor configured to detect sleep cycles associated with the user 102, a sensor configured to detect eye movements of the user 102, a sensor configured to detect breath of the user 102, and so on. In some instances, the detection component 104 further includes other types of sensors configured to detect physiological parameters that reflect the respiration state associated with the user 102 such as a flow rate sensor configured to detect an airway flow rate associated with the user 102, a pressure sensor configured to detect an airway pressure associated with the user 102, and so on. Additionally, the other types of sensors configured to detect physiological parameters that reflect the respiration state associated with the user 102 may be integrated into the administration component 106. In some instances, the detection component 104 further includes other types of sensors such as a body temperature sensor configured to detect a body temperature, a chest strap configured to detect ECG, a helmet or head worn device configured to detect brain waves/activity, a sound sensor configured to detect a sound/noise level associated with the user 102, and so on.

In some instances, the detection component 104 includes a wearable device that is attached to or worn by the user 102's body. For example, the wearable device can a smartwatch, a smart bracelet, smart glasses, smart clothing, smart footwear, a smart armband, a smart belt, smart ring, smart earphone, a chest strap configured to detect a heart rate and/or ECG, a helmet, cap, or headband configured to detect brain waveforms/activity, etc. In some instances, the one or more sensors are attached to or embedded in the wearable device.

The administration component 106 is configured to automatically administer a psychoactive substance to a respiratory system (e.g., the nose, the mouth, the respiratory tract, the lungs) of the user 102 based on detection of a trigger. In certain implementations, the trigger includes brain waves associated with sleep cycles, dream states, A-HA experiences the occurrence of learning, REM sleep, non-REM sleep, involuntary body movement of a user, voluntary body movement of a user, heart rate meeting a threshold, blood oxygen saturation meeting a threshold, respiration rate meeting a threshold, body temperature meeting a threshold, skin galvanics meeting a threshold, location of a user generally, location of a user in relation to a starting location, out of body experience, distance traveled, velocity of movement, event in a virtual reality setting, event during game play, ingestion of a beverage or food product, gastric content, gastric distress, air humidity level, ambient sound level, changed light level, any combination thereof, and so on. In some instances, the administration component 106 is configured to administer a series of doses of psychoactive substance to the respiratory system of the user 102 based on a dosing schedule when one or more triggers are detected.

In implementations, the dosing schedule includes information regarding, for a particular system and user, the type of the airflow component, a type of the psychoactive substance to be administered, a dose of the psychoactive substance to be administered, the timing to administer the dose of the psychoactive substance in relation to detection of the trigger, the corresponding relationship thereof, and so on. In some instances, the dosing schedule includes a specific time for each dose to be administered. In some instances, the dosing schedule includes the duration of each dose to be administered in relation to the trigger. In some instances, the dosing schedule includes the time interval of two doses to be administered. In some instances, the dosing schedule is received by the administration component 106 from other devices such as a terminal device 122.

As an example, upon detection of a trigger which is alpha and beta brain waves associated with the user 102 indicating sleep onset (relaxation phase) of the user 102, the administration component 106 administers gamma-aminobutyric acid (GABA), theanine, linalool, *Melissa officinalis* essential oil (including phenolic compounds such as rosmarinic acid and caffeic acid derivatives), delta-8 THC: delta-9 THC with 1:1 ratio, and/or cannabis terpenes containing at least 1% linalool by mass of the entire terpene fraction to the respiratory system of the user 102 according to the dosing schedule.

As another example, upon detection of a trigger which is delta brain waves associated with the user 102 indicating deep sleep of the user 102, the administration component 106 administers *Valeriana officinalis* and compounds thereof, *Humulus lupulus* and compounds thereof, *Rosmarinus officinalis* essential oil and compounds thereof, and/or cannabidiol (CBD) to the respiratory system of the user 102 according to the dosing schedule.

As yet another example, upon detection of a trigger which is Non-REM sleep of the user 102, the administration component 106 administers *Valeriana officinalis* and compounds thereof, *Humulus lupulus* and compounds thereof, *Rosmarinus officinalis* essential oil and compounds thereof, and/or cannabidiol (CBD) to the respiratory system of the user 102 according to the dosing schedule.

As yet another example, upon detection of a trigger which is sleep spindles, the administration component 106 administers *Valeriana officinalis* and compounds thereof, *Humulus lupulus* and compounds thereof, *Rosmarinus officinalis* essential oil and compounds thereof, and/or cannabidiol (CBD) to the respiratory system of the user 102 according to the dosing schedule.

As yet another example, upon detection of a trigger which is REM sleep of the user 102, the administration component 106 administers galantamine and compounds, especially sesquiterpene lactones, found in *Calea zacatechichi* or *Calea ternifolia* (e.g. calaxin, ciliarin, calein A-F, calealactones and caleachromenes) to the respiratory system of the user 102 according to the dosing schedule.

As yet another example, upon detection of a trigger which is brain waves associated with dream states of the user 102, the administration component 106 administers galantamine and compounds, especially sesquiterpene lactones, found in *Calea zacatechichi* or *Calea ternifolia* (e.g. calaxin, ciliarin, calein A-F, calealactones and caleachromenes) to the respiratory system of the user 102 according to the dosing schedule.

As yet another example, upon detection of a trigger which is involuntary body movement of a user 102, the administration component 106 administers GABA, theanine, linalool, and *Melissa officinalis* essential oil (including phenolic compounds such as rosmarinic acid and caffeic acid derivatives), delta-8 THC: delta-9 THC with 1:1 ratio, and/or cannabis terpenes containing at least 1% linalool by mass of the entire terpene fraction to the respiratory system of the user 102 according to the dosing schedule.

As yet another example, upon detection of a trigger which is an A-HA brain wave (theta waves, or a spike in anterior cingulate cortical activity), the administration component 106 administers small, transient doses of the classical (psilocybin, mescaline, LSD) and non-classical (DMT, 5-MeO-DMT, salvinorin) psychedelics to the respiratory system of the user 102 according to the dosing schedule. In implementations, achieving the A-HA state is often achieved by breaking an especially high gamma rhythm pattern. Gamma rhythm pattern is associated with focused attention. Decreasing gamma rhythm pattern is similar to stimulating lateral thinking or creativity. One way to decrease gamma rhythm pattern is to administer small, transient doses of the classical (psilocybin, mescaline, LSD) and non-classical (DMT, 5-MeO-DMT, salvinorin) psychedelics to the respiratory system of the user 102.

As yet another example, upon detection of a trigger which is voluntary body movement of the user 102 (e.g., movement of eye(s), hand(s), arm(s), head, foot/feet, leg(s), and/or torso of the user 102), the administration component 106 administers GABA, theanine, linalool, and *Melissa officinalis* essential oil (including phenolic compounds such as rosmarinic acid and caffeic acid derivatives), delta-8 THC: delta-9 THC with 1:1 ratio, and/or cannabis terpenes containing at least 1% linalool by mass of the entire terpene fraction to the respiratory system of the user 102 according to the dosing schedule.

As yet another example, upon detection of a trigger which is a heart rate of the user 102 meeting a threshold, the administration component 106 administers cannabidiol. to the respiratory system of the user 102 to decrease resting systolic blood pressure (BP) and stroke volume of the user 102 according to the dosing schedule.

As yet another example, upon detection of triggers which include a blood oxygen saturation of the user 102 decreasing to a certain threshold, a respiration rate of the user 102 increasing to a certain threshold, a body temperature of the user 102 increasing to a certain threshold, and skin galvanics of the user 102 increasing to a certain threshold, the administration component 106 administers THC to the respiratory system of the user 102 according to the dosing schedule. In implementations, the blood oxygen saturation of the user 102, the respiration rate of the user 102, the body temperature of the user 102, and the skin galvanics of the user 102 may indicate a fear response of the user 102, and administration of THC may increase the perception of anxiety and push oxytocin to decrease the perception of fear of the user 102.

As yet another example, upon detection of trigger which indicates an out of body experience of the user, the administration component 106 administers ketamine or salvia *divinorum* (salvinorin A) to the respiratory system of the user 102 according to the dosing schedule.

As yet another example, upon detection of a trigger which is gastric content of the user 102 in a certain range, the administration component 106 administers THCV to the respiratory system of the user 102 according to the dosing schedule. In implementations, the administration of THCV may conduct vagus nerve stimulation to trigger the parasympathetic nervous system (i.e. rest and digest), mechanical induction of deep-breathing over shallow-breathing, and/or anorectic effect.

As yet another example, upon detection of a trigger which is gastric distress of the user 102 in a certain range, the administration component 106 administers chamomile, ginger, licorice, mint and cannabigerol (CBG) to the respiratory system of the user 102 according to the dosing schedule.

As yet another example, upon detection of a trigger which is an air humidity level of the environment increasing to a certain level, the administration component 106 administers shilajit to the respiratory system of the user 102 according to the dosing schedule.

As yet another example, upon detection of triggers which include ambient oxygen level decreasing to a certain level, the elevation increasing to a certain level, and/or ultra violet (UV) increasing to a certain level, the administration component 106 administers shilajit to the respiratory system of the user 102 according to the dosing schedule.

As yet another example, upon detection of a trigger which is ambient sound level increasing/decreasing to a certain level, the administration component 106 administers decreased/increased glutamate (add exogenous MSG) to the respiratory system of the user 102 according to the dosing schedule. In implementations, increased glutamate (add exogenous MSG) may induce greater sensitivity to sound by the user 102, and decreased/blocked glutamate may cause less sensitivity to sound of the user 102. Additionally, or alternatively, exogenous GABA, theanine, or Withania somnifera (Ashwagandha) can be administered.

As yet another example, upon detection of a trigger which is changed light level, the administration component 106 administers melatonin, adenosine, and/or caffeine to the respiratory system of the user 102 according to the dosing schedule. In response to a simulated night cycle (decreased light level), melatonin and adenosine can be administered to the user 102. In response to a simulated day cycle (increased light level), adenosine to be administered to the user 102 may be decreased, and caffeine to be administered to the user 102 may be increased.

In some instances, the psychoactive substance includes a constituent that alters a psychoactive state associated with the user. In some instances, the psychoactive substance includes a constituent that alters a sleep state associated with the user. In some instances, the psychoactive substance includes a constituent that alters a respiration state associated with the user such as an airway flow rate associated with the user, an airway pressure associated with the user, and so on. In some instances, the psychoactive substance includes a psychoactive substance, as defined elsewhere herein.

The administration component 106 includes a storage component 108 and a control component 110. The storage component 108 is configured to store a psychoactive substance to administer in the event a trigger is detected. In some instances, the storage component 108 may have cartridges, reservoirs, containers, bottles, any other types of storage suitable for storing the psychoactive substance, and so on. In some instances, the storage component 108 may include individual units that can store different psychoactive substances separately.

In implementations, when the administration component 106 is administering the psychoactive substance to the respiratory system of the user 102 based on the dosing schedule, the detection component 104 may keep detecting one or more triggers. Upon the detection of one or more different triggers, the administration component 106 is configured to change the administration of the psychoactive substance to the respiratory system of the user 102 based on the dosing schedule. In some instances, upon detection of one or more different triggers, the administration component 106 may switch to administer a different psychoactive substance based on the dosing schedule. In some instances, upon detection of one or more different triggers, the administration component 106 may increase or decrease the number of doses of the psychoactive substance based on the dosing schedule. In some instances, upon detection of one or more different triggers, the administration component 106 may increase or decrease the time interval between administering two doses based on the dosing schedule. In some instances, the administration component 106 may increase or decrease the duration of doses based on the dosing schedule. In some instances, the administration component 106 may add or delete one or more doses based on the dosing schedule. In some instances, the administration component 106 may change the timing of doses based on the dosing schedule.

As an example, during administering melatonin and/or adenosine to the user 102, the detection component 104 keeps detecting one or more triggers. Upon detection of a simulated day cycle (increased light level), the administration component 106 may administer an decreased dose melatonin and/or a decreased dose of adenosine to the user 102, and an increased dose of caffeine to the user 102 based on the dosing schedule.

As another example, during or after administering 4 mg/hour of cannabinoid to the user 102, the detection component 104 continues to detect one or more triggers. Upon continued detection of the one or more triggers, the administration component 106 administers a dose of 5 mg/hour of cannabinoid to the user 102 based on the dosing schedule.

The control component 110 is further configured to store a dosing schedule in a memory. For example, the dosing schedule may be stored in a dosing schedule database in the memory. In some instances, the control component 110 includes the memory which may have hard drives, floppy diskettes, optical disks, read-only memories (ROMs), random access memories (RAMs), erasable programmable ROMs (EPROMs), electrically erasable programmable ROMs (EEPROMs), non-volatile memory such as flash memory, magnetic or optical cards, solid-state memory devices, or other types of physical media suitable for storing electronic instructions.

As described above, the one or more triggers can include one or more physiological parameters meeting one or more conditions. In implementations, the one or more conditions include whether a physiological parameter is above, equal to, or below a threshold, and/or whether a physiological parameter falls within a range. In some instances, there may be one or more thresholds/ranges received by the administration component 106 from other devices. In implementations, the detection component 104 determines whether the one or more triggers are detected based on the one or more thresholds/ranges.

As an example, the one or more thresholds/ranges include a first threshold for a heart rate of 90 beats per minute, a second threshold for blood oxygen saturation of 80%, a third threshold for increased body movement of 40%, and a fourth range defining brain waves indicative of REM sleep. For instance, a first physiological parameter associated with the user 102 which is a heart rate associated with the user 102 is detected as 100 beats per minute. A second physiological parameter associated with the user 102 which is a blood oxygen saturation associated with the user 102 is detected as 70%. A third physiological parameter associated with the user 102 which is an increased amount of body movement associated with the user 102 is detected as 50%. A fourth physiological parameter associated with the user 102 is brain waves indicative of REM sleep. The detection component 104 compares the first physiological parameter which is a heart rate of 100 beats per minute with the first threshold for a heart rate of 90 beats per minute, and determines that first physiological parameter is above the first threshold, and determines that a trigger is detected. The detection component 104 compares the second physiological parameter which is the blood oxygen saturation of 70% with the second threshold for blood oxygen saturation of 80% and determines that the second physiological parameter is below the second threshold and determines that a trigger is detected. The detection component 104 compares the third physiological parameter which is an increased amount of body movement of 50% with the third threshold for increased body movement of 40%, and determines that the third physiological parameter is above the third threshold, and determines that a trigger is detected. The detection component 104 compares the fourth physiological parameter which is brain waves indicative of REM sleep and determines that the fourth physiological parameter is within the fourth range and determines that a trigger is detected.

The control component 110 can be further configured to store a user database. As an example, the user database includes a username, dosing schedules associated with the user, a list of triggers, and at least one dose to be administered upon detection the triggers. The triggers may include brain signal patterns associated with sleep cycles, dream states, A-HA experiences, the occurrence of learning, REM sleep, Non-REM sleep, involuntary body movement of a user, voluntary movement of a user, heart rate meeting a threshold, blood oxygen saturation meeting a threshold, respiration rate meeting a threshold, body temperature meeting a threshold, skin galvanics meeting a threshold, location of a user generally, location of a user in relation to a starting location, distance traveled, velocity of movement, event in a virtual reality setting, event during game play, ingestion of a beverage or food product, gastric content, air humidity level, ambient sound level, changed light level, an out of body experience and so on. In some instances, the triggers may be defined in any combination. In some instances, the detection of triggers may be determined based on thresholds/ranges by the detection component 104. Additional details of such databases are provided throughout this disclosure.

The administration component 106 can further include an airway component 112 and an introducing component 114 in fluid communication with the airway component 112. The airway component 112 is configured to provide an airflow to the respiratory system of the user 102. In some instances, the administration component 106 and the airway component 112 form a system that may be implemented in various ways including a CPAP machine, a nasal cannula, a venturi mask, a nebulizer, a non-rebreather mask, an anesthetic facemask, a humidifier, a ventilator, and/or other devices capable of providing airflow to the respiratory system of the user 102. FIG. 1 depicts an example of an administration component 106 and an airway component 112 implemented as a CPAP machine, but it is to be appreciated that these components can take many forms.

The introducing component 114 is configured to introduce the psychoactive substance into the airflow provided by the airway component 112. The introducing component 114 is further configured to introduce the psychoactive substance into the airflow in, for example, a vaporized form, in droplets, and/or in an aerosolized form. In some instances, the introducing component 114 includes a vaporizer configured to vaporize the psychoactive substance. In some instances, the introducing component 114 includes an atomizer configured to atomize the psychoactive substance. In some instances, the introducing component 114 includes an aerosolizer configured to aerosolize the psychoactive substance. Additionally, the introducing component 114 further includes a cartridge (not shown) to accommodate the psychoactive substance. In implementations, the introducing component 114 may connect to another part of the administration component 106 at a junction 116. The introducing component 114 may include a tube 118 configured to deliver the airflow to the user 102 and a mask 120 worn on the user's face. The introducing component 114 may be arranged at many locations. In some instances, the introducing component 114 is disposed near the junction 116 where the airflow component 112 is coupled to another part of the administration component 106. In some instances, the introducing component 114 is arranged within the airway component 112 (e.g., within the tube 118 of the airway component 112). In some instances, the introducing component 114 is arranged within the mask 120 worn on the user's face.

The system 100 may further include a terminal device 122 in communication with the detection component 104 and the administration component 106. In some instances, the terminal device 122 is in wireless communication with the detection component 104 and the administration component 106, for example, through RF, IR, microwave, Bluetooth, Wi-Fi, and so on. In some instances, the terminal device 122 is in wired communication with the detection component 104 and the administration component 106, for example, through hardwired connection, cable, fiber-optic, and so on. Other types of communication may be used, and this disclosure is not limited thereto.

The terminal device 122 can be configured to execute an application (App) and present a user interface. The user 102 may log in to the App. The user interface is configured to allow the user 102 to make one or more changes to the dosing schedule by providing user input via the user interface. For example, the user may input information to the terminal device 122 via keyboards, touchpads, touch screens, mouses, scanners, cameras, joysticks, microphones, chip readers, stylus, and/or light pens. In implementations, other types of input devices may be used for the user to input information to the terminal device 122, and this disclosure is not limited thereto.

The terminal device 122 includes a memory. In certain examples, the memory is configured to store information associated with the user 102 in a user database (for example instead of or in addition to a user database found within a control component). For example, the memory is configured to store the user profile information associated with the user 102 in the user database. In some instances, the memory is one or more of an electronic storage medium, a magnetic storage medium, an optical storage medium, a quantum storage medium, and so forth. For example, the memory includes hard drives, floppy diskettes, optical disks, ROMs, RAMs, EPROMs, EEPROMs, non-volatile memory (e.g., flash memory), magnetic or optical cards, solid-state memory devices, or other types of physical media suitable for storing electronic instructions. The user profile information associated with the user 102 may include passwords and permissions as well as past measured physiological parameters and doses of the psychoactive substance administered to the user 102.

The terminal device 122 can be further configured to receive the dosing schedule from the user 102. In some instances, the terminal device 122 is configured to receive the dosing schedule from a researcher or caregiver associated with the user 102 such as a family member, nurse, or doctor. For example, the terminal device 122 receives a dosing schedule where a 5 mg/hour dose of cannabinoids is to be administered to the user 102 upon detection of certain triggers and a 10 mg/hour dose of cannabinoids is to be administered upon detection of different triggers. The terminal device 122 is further configured to send the dosing schedule to the administration component 106.

The terminal device 122 is further configured to receive the one or more physiological parameters from the detection component 104. For example, terminal device 122 receives data indicating a heart rate of 100 beats per minute, a blood oxygen saturation of 70%, and a brain wave associated with the user 102 from the detection component 104.

The terminal device 122 is further configured to receive the one or more thresholds/ranges such as a first threshold which is a heart rate of 90 beats per minute, a second threshold which is a blood oxygen saturation of 80%, and a third range which defines brain waves indicative of REM sleep from the user 102. For example, the user 102 may select and/or input the one or more thresholds/ranges via the user interface to the terminal device 122. As another example, the thresholds/ranges may be set and/or input by a researcher or caregiver associated with the user 102. The terminal device 122 is further configured to send the one or more thresholds/ranges to the administration component 106.

The terminal device 122 is further configured to display, via the user interface, the dosing schedule, the one or more physiological parameters, the one or more triggers, and/or the one or more thresholds/ranges, and so on. The user 102, the researcher, or the caregiver associated with the user 102 may review the dosing schedule, the one or more physiological parameters, the one or more triggers, and/or the one or more thresholds/ranges displayed on the user interface.

The terminal device 122 is further configured to receive, via the user interface, one or more changes to the dosing schedule. In implementations, the user 102 may make changes to the dosing schedule via the user interface of the terminal device 122. For example, the user 102 may increase/decrease the thresholds, adjust the ranges, alter the triggers, etc. In some instances, the user 102 may change the dosing schedule by increasing or decreasing doses, increasing, or decreasing intervals between doses, increasing, or decreasing durations of doses, and/or altering triggers when the doses are to be administered.

The terminal device 122 is further configured to send data associated with a changed dosing schedule to the administration component 106. Accordingly, the administration component 106 which is in communication with the terminal device 122 is further configured to receive and store the data associated with the changed dosing schedule.

The terminal device 122 is further configured to send the dosing schedule, the one or more thresholds/ranges, and/or the one or more physiological parameters to a device associated with the researcher or caregiver associated with the user 102. For example, the terminal device 122 sends the dosing schedule that has been administered throughout the night to the device associated with the researcher or caregiver associated with the user 102 in the morning. Accordingly, the researcher or caregiver associated with the user 102 can verify the doses of the psychoactive substance administered to the user throughout the night.

In some instances, the terminal device 122 is an electronic device utilized by the user 102, the researcher or caregiver associated with the user 102. The user 102, the researcher, or the caregiver associated with the user 102 may use the terminal device 122 to interact with the administration component 106. The terminal device 122 may be a mobile phone, a tablet, a computer, a proprietary or purpose-built terminal, etc. For example, the user 102 may view details regarding the dosing schedule, the past and/or current physiological parameters measured by the detection component 104, and/or the one or more thresholds/ranges via the interface of the terminal device 122. The user 102 may select or make changes to the dosing schedule via the user interface of the terminal device 122. As another example, the terminal device 122 may be utilized by the researcher or caregiver associated with the user 102 in the same manner as described for the user 102.

Additionally, some features of the terminal device 122 may have differential accessibility to the user 116, the researcher, or the caregiver associated with the user 102. For example, the researcher or caregiver associated with the user 102 can make changes to the dosing schedule while the user 102 cannot change the dosing schedule.

The system 100 is further configured to communicate with a cloud platform 124. For example, each of the detection component 104, the administration component 106, and the terminal device 122 may be configured to communicate with the cloud platform 124. In implementations, the communication between the cloud platform 124 and each of the detection component 104, the administration component 106, and the terminal device 122 may be through a wireless network or a wired network, and this disclosure is not limited thereto. In some instances, the cloud platform 124 is a distributed network including multiple servers which serve as compute nodes and storage nodes. Computational or storage tasks may be distributed across any number of the nodes of the cloud platform 124 allowing for improved access and processing speeds. The redundancy of the cloud platform 124 may provide improved reliability. The cloud platform 124 may be private, such that access is limited by encryption, other security methods, or being physically isolated from the Internet. The cloud platform 124 may be public and widely available. A public cloud platform may additionally feature encryption and other security means though may be more widely accessible than a private cloud platform.

With the system 100, a psychoactive substance may be automatically administered based on the detection of a trigger. The system 100 allows the administration of a psychoactive substance to the user while the user sleeps. The dose of the psychoactive substance can be finely controlled based on detection of a trigger throughout the time course of the user's sleep. In certain examples, the user may gain and maintain a restful sleep pattern. In certain examples, the user may experience lucid dreaming.

Figure 2A:
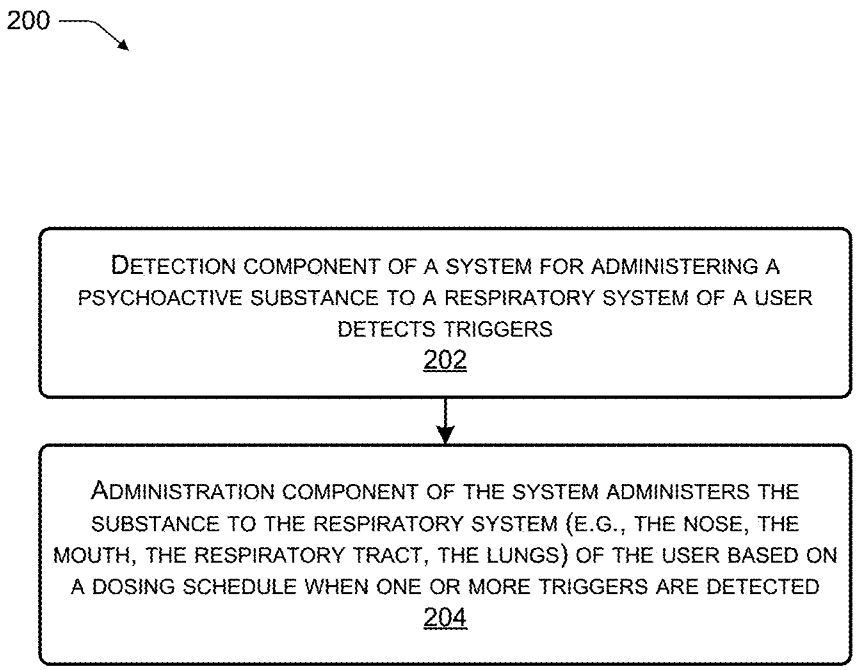
FIGS. 2A-2C illustrate a flowchart of example processes for administering a psychoactive substance to a user during sleep based on a detected trigger according to implementations of this disclosure.
Figure 2B:
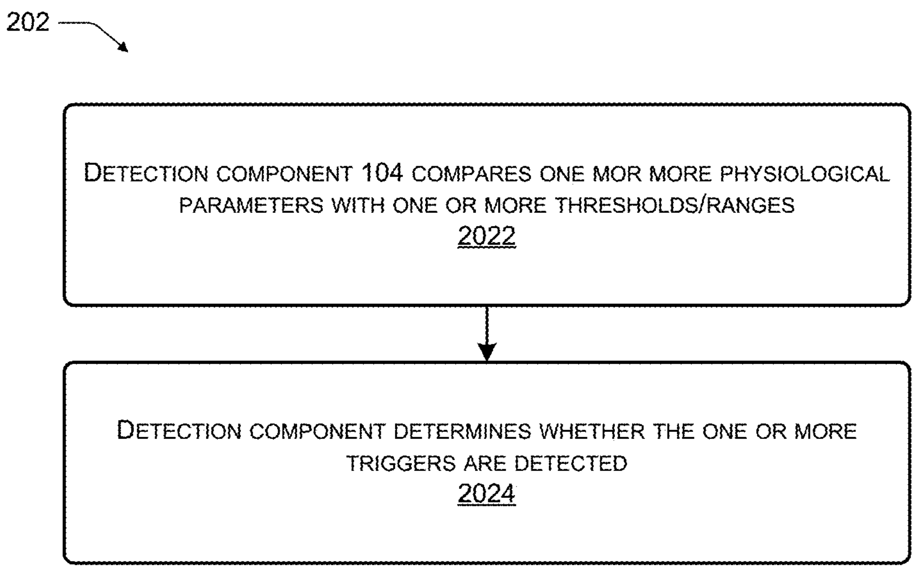
Figure 2C:
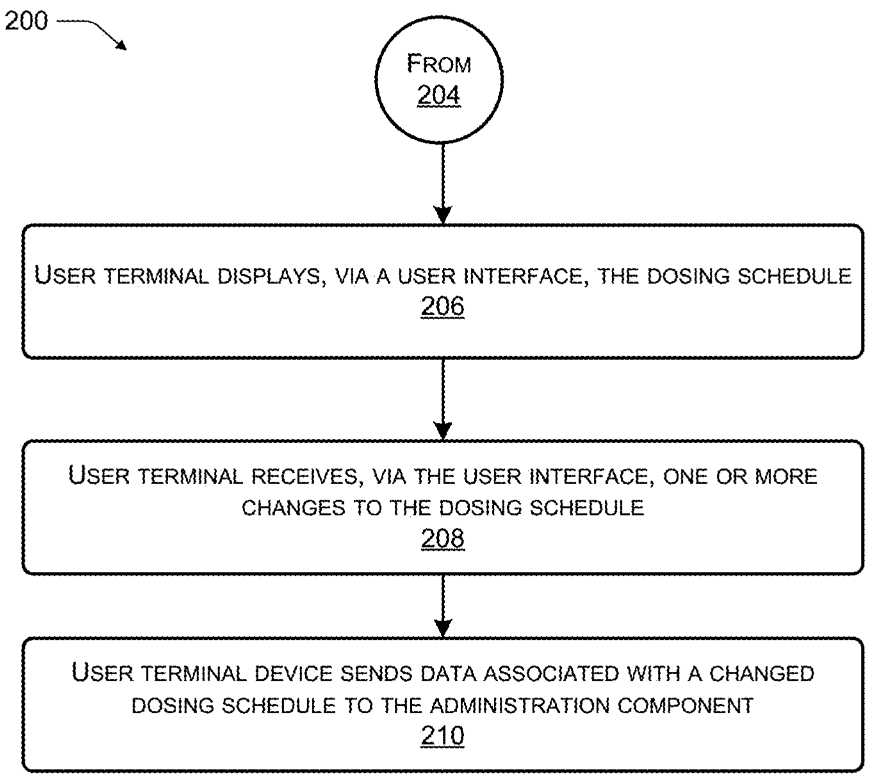

FIG. 2A, FIG. 2B, and FIG. 2C illustrate a flowchart of an example process 200 for administering a psychoactive substance to a user according to implementations of this disclosure. Referring to FIG. 2A, the process 200 includes the following: at 202, a detection component of a system for administering a psychoactive substance to a respiratory system of a user detects triggers. In implementations, the system for administering a psychoactive substance to a respiratory system of a user may be the system 100 as described above. In implementations, the triggers include occurrence of a pre-set event or a pre-set condition being met. In some instances, the triggers include one or more physiological parameters associated with the user meeting a certain condition, for example, reaching a threshold, and/or falling within a range. The certain condition can be pre-set by a system, or can be selected by a user, researcher, or in certain circumstances, by a professional (e.g., a therapist, nurse, or doctor). In some instances, the one or more physiological parameters associated with the user include a brain wave associated with the user, a heart rate associated with the user, a blood oxygen saturation associated with the user, and/or an amount of body movement associated with the user. In some instances, the body movement includes the movement of eye(s), hand(s), arm(s), head, foot/feet, leg(s), and/or torso of the user. In some instances, the one or more physiological parameters associated with the user further includes other physiological parameters that reflect sleep cycles associated with the user, and so on. In some instances, the one or more physiological parameters associated with the user further include other physiological parameters that reflect the sleep state of the user. In some instances, the one or more physiological parameters associated with the user further include other physiological parameters that reflect the respiration state associated with the user such as an airway flow rate associated with the user, an airway pressure associated with the user, and so on. In some instances, the one or more physiological parameters associated with the user further include a body temperature associated with the user, an ECG associated with the user, brain waves/activity associated with the user, a sound/noise level associated with the user, and so on.

At 204, an administration component of the system administers the psychoactive substance to the respiratory system (e.g., the nose, the mouth, the respiratory tract, the lungs) of the user based on a dosing schedule when one or more triggers are detected. Additional details regarding how the administration component administers the psychoactive substance are described with reference to FIG. 1.

In some instances, the psychoactive substance includes a constituent that alters a psychoactive state associated with the user. In some instances, the psychoactive substance includes a constituent that alters a sleep state associated with the user. In some instances, the substance includes a constituent that alters a respiration state associated with the user such as an airway flow rate associated with the user, an airway pressure associated with the user, and so on. The psychoactive substance is a psychoactive substance, as defined elsewhere herein.

Referring to FIG. 2B, operations of 202 further include the following: at 2022, the detection component 104 compares one more physiological parameters with one or more thresholds/ranges. As described above, the one or more triggers include one or more physiological parameters meeting one or more conditions. In implementations, the one or more conditions include whether a physiological parameter is above, equal to, or below a threshold, and/or whether a physiological parameter falls within a range. As an example, the one or more thresholds/ranges include a first threshold for a heart rate of 90 beats per minute, a second threshold for blood oxygen saturation of 80%, a third threshold for increased body movement of 40%, and a fourth range defining brain waves indicative of REM sleep. For instance, a first physiological parameter associated with the user 102 which is a heart rate associated with the user 102 is detected as 100 beats per minute. A second physiological parameter associated with the user 102 which is a blood oxygen saturation associated with the user 102 is detected as 70%. A third physiological parameter associated with the user 102 which is an increased amount of body movement associated with the user 102 is detected as 50%. A fourth physiological parameter associated with the user 102 is brain waves indicative of REM sleep. The detection component 104 compares the first physiological parameter which is a heart rate of 100 beats per minute with the first threshold for a heart rate of 90 beats per minute and determines that first physiological parameter is above the first threshold. The detection component 104 compares the second physiological parameter which is the blood oxygen saturation of 70% with the second threshold for blood oxygen saturation of 80% and determines that the second physiological parameter is below the second threshold. The detection component 104 compares the third physiological parameter which is an increased amount of body movement of 50% with the third threshold for increased body movement of 40% and determines that the third physiological parameter is above the third threshold. The detection component 104 compares the fourth physiological parameter which is brain waves indicative of REM sleep.

At 2024, the detection component determines whether the one or more triggers are detected. For example, when a first physiological parameter associated with the user (such as a heart rate associated with the user) is above a first threshold (such as 90 beats per minute), the detection component determines that a trigger is detected. As another example, when a second physiological parameter associated with the user (such as a brain wave associated with the user) is within a range (such as brain waves indicative of REM sleep), the control component determines that a trigger is detected. In implementations, the triggers may be used in any combination.

Referring to FIG. 2C, the process 200 further includes the following: at 206, a user terminal displays, via a user interface, the dosing schedule. In some instances, the user terminal is further configured to display, via the user interface, the one or more physiological parameters, the one or more triggers, and/or the one or more threshold values. In implementations, the terminal device may be a mobile phone, a tablet, a computer, a proprietary or purpose-built terminal, etc. For example, the user may view details about the dosing schedule, the past and/or current physiological parameters measured by the detection component.

At 208, the user terminal receives, via the user interface, one or more changes to the dosing schedule. The user may select or make changes to the dosing schedule via the user interface of the terminal device. As another example, the terminal device may be utilized by the researcher or caregiver associated with the user in the same manner as described for the user. Additionally, some features of the terminal device may have differential accessibility to the user and the researcher or caregiver associated with the user. For example, the researcher or caregiver can make changes to the dosing schedule while the user cannot change the dosing schedule. For example, the user may input information to the terminal device via keyboards, touchpads, touch screens, mouses, scanners, cameras, joysticks, microphones, chip readers, stylus, and/or light pens. In implementations, other types of input devices may be used for the user to input information to the terminal device, and this disclosure is not limited thereto.

At 210, the user terminal sends data associated with a changed dosing schedule to the administration component. The administration component may receive the data associated with the changed dosing schedule from the terminal device, and store data associated with the changed dosing schedule in the memory. The administration component may administer the psychoactive substance to the respiratory system of the user based on the changed dosing schedule.

With the process 200, a psychoactive substance can be automatically administered based on the detection of a trigger. The process 200 allows the administration of a psychoactive substance to the user while the user sleeps. The dose of the psychoactive substance can be finely controlled following detection of a trigger throughout the time course of the user's sleep. In certain examples, the user may gain and maintain a restful sleep pattern. In certain examples, the user may experience lucid dreaming.

FIG. 3 illustrates an example dosing schedule 300 according to implementations of this disclosure. Referring to FIG. 3, column 302 shows the dose of the psychoactive substance to be administered, and column 304 shows the type of airflow component to administer the dose of the psychoactive substance. Row 306 indicates that a dose of 5 mg of the psychoactive substance is to be administered by a CPAP device. Row 308 indicates that a dose of 5 mg of the psychoactive substance is to be administered by an air humidifier. Row 310 indicates that a dose of 5 mg of the psychoactive substance is to be administered by an oxygen therapy nasal cannula. Row 312 indicates that a dose of 5 mg of the psychoactive substance is to be administered by a non-rebreather mask kit. Row 314 indicates that a dose of 5 mg of the psychoactive substance is to be administered by a room humidifier.

Column 316 shows the dose of the psychoactive substance to be administered, and column 318 shows the timing to administer the dose of the psychoactive substance. Row 320 indicates that from 11 pm to 4 am, a dose of 5 mg of the psychoactive substance is to be administered if a trigger is detected. Row 322 indicates that from 4 am to 6 am, a dose of 10 mg of the psychoactive substance is to be administered if a trigger is detected.

Though the example dosing schedule 300 shows specific doses, timings, and type of airflow components, this disclosure is not limited thereto. In some instances, the dosing schedule 300 may include the time interval of two doses to be administered. For example, the dosing schedule 300 may indicate that upon detection of brain waves indicative of REM sleep of the user, a certain amount of the psychoactive substance is to be administered. Additionally, the dosing schedule 300 may include other types of airway components that are configured to provide an airflow to the respiratory system of the user.

With the dosing schedule 300, a psychoactive substance can be automatically administered upon the detection of a trigger. The dosing schedule 300 allows the administration of a psychoactive substance to the user while the user sleeps. The dose of the psychoactive substance can be finely controlled following detection of a trigger throughout the time course of the user's sleep. In certain examples, the user may gain and maintain a restful sleep pattern. In certain examples, the user may experience lucid dreaming.

FIG. 4 illustrates an example database 400 according to implementations of this disclosure. In some instances, the database 400 is associated with a particular user. Referring to FIG. 4, the database 40400 stores the username, the date, and the corresponding relationship among the timing, the dose, and the trigger (e.g., a physiological parameter). Column 402 shows that at 10 pm, 5 mg of the psychoactive substance is administered with a heart rate of 90 beats per minute, blood oxygen saturation ($SpO_2$) of 80%, and increased body movement. Column 404 shows that at 11 pm, 5 mg of the psychoactive substance is administered with a heart rate of 90 beats per minute, $SpO_2$ of 80%, and increased body movement. Column 406 shows that at 12 am, 5 mg of the psychoactive substance is administered with a heart rate of 90 beats per minute, $SpO_2$ of 80%, and increased body movement. Column 408 shows that at 1 am, 5 mg of the psychoactive substance is administered with the heart rate of 90 beats per minute, $SpO_2$ of 80%, and an increased body movement. Column 410 shows that at 2 am, 5 mg of the psychoactive substance is administered with a heart rate of 90 beats per minute, $SpO_2$ of 80%, and an increased body movement. Column 412 shows that at 3 am, 5 mg of the psychoactive substance is administered with the heart rate of 90 beats per minute, $SpO_2$ of 80%, and an increased body movement. Column 414 shows that at 4 am, 5 mg of the psychoactive substance is administered with the heart rate of 100 beats per minute, $SpO_2$ of 80%, and increased body movement. Column 416 shows that at 5 am, 10 mg of the psychoactive substance is administered with a heart rate of 100 beats per minute, $SpO_2$ of 80%, and increased body movement. The heart rate, the blood oxygen saturation, and the body movement may be provided by the detection component 104. In some instances, the body movement includes the movement of eye(s), hand(s), arm(s), head, foot/feet, leg(s), and/or torso of the user.

While this description provides a simple example of embodiments disclosed herein, it does not reflect two important optional aspects: 1) the ability to use collections of stimuli, or stimuli patterns, to elicit a response and 2) a timing component that allows careful "programming" of the administration of the psychoactive substance taking into effect pharmacokinetic aspects of the substance and the route of administration to align the effects of the psychoactive substance with certain brain patterns or stages of various conscious states that predictably follow one another, e.g. stage 2 NREM that show predictable occurrences. Further, although the example database 400 shows specific timings, doses, and physiological parameters, this disclosure is not limited thereto. In some instances, the database 400 may include other physiological parameters that reflect the sleep state of the user.

Figure 5:
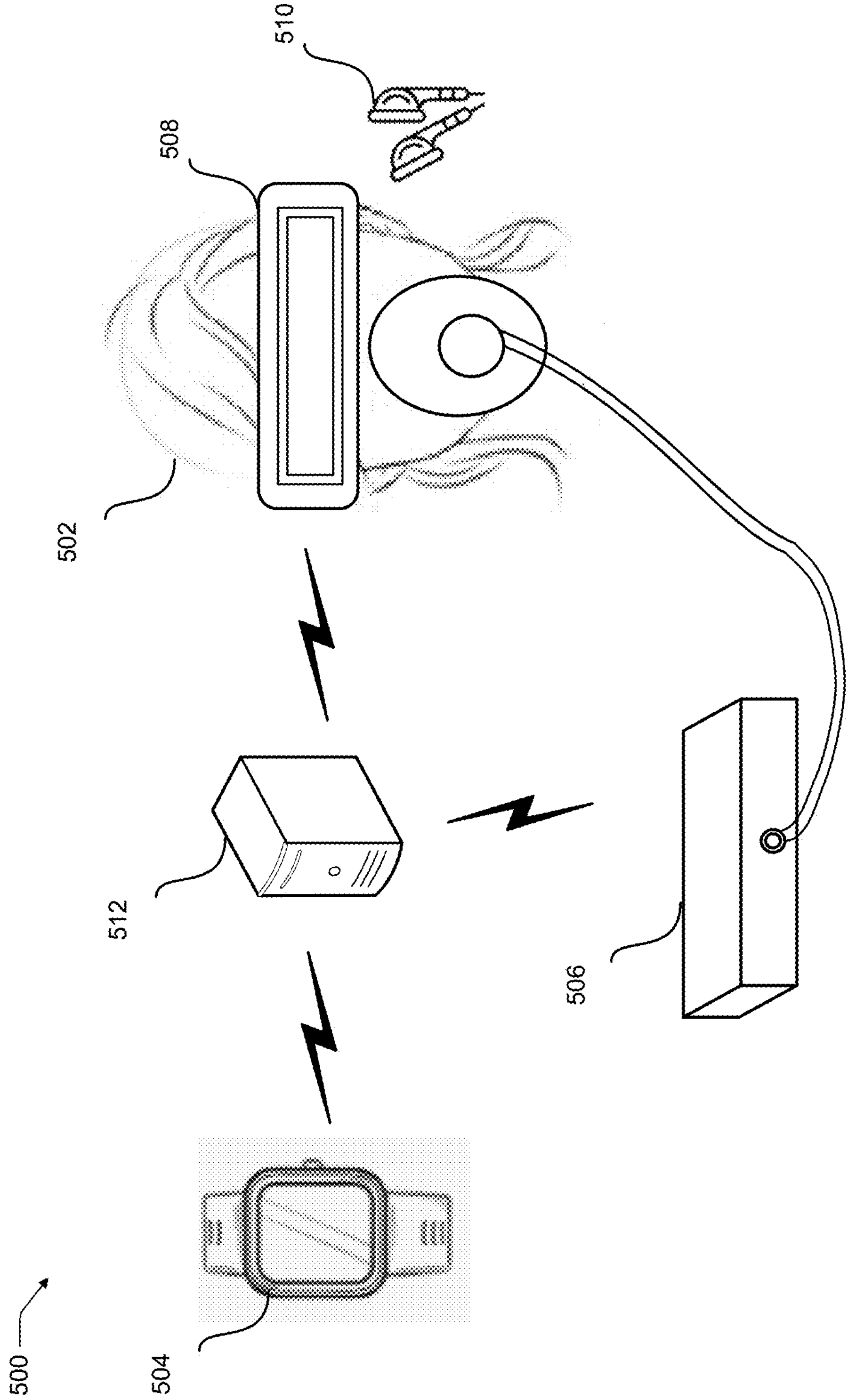
FIG. 5 illustrates an exemplary system for automatically administering a psychoactive substance to a user based on a detected trigger when the user is immersed in an environment created by a virtual reality device.

FIG. 5 illustrates an example system 500 for establishing a virtual/augmented reality environment for a user 502 according to implementations of this disclosure. Referring to FIG. 5, the system 500 includes a detection component 504, an administration component 506, a visualization component 508, an audio component 510, and a terminal device 512 in communication with the detection component 504, the administration component 506, and the visualization component 508. In some instances, the detection component 504, the administration component 506, the visualization component 508, and the audio component 510 are in communication with the terminal device 512 wirelessly, for example, through radio broadcast (RF), infrared (IR), microwave, Bluetooth, Wi-Fi, and so on. In some instances, the detection component 504, the administration component 506, the visualization component, and the audio component 510 are in communication with the terminal device 512 wiredly, for example, through hardwired connection, cable, fiber-optic, and so on.

The detection component 504 is configured to detect triggers, for example, selected events or conditions. In some instances, the triggers include occurrence of a pre-set event or a pre-set condition being met. In some instances, the triggers include one or more physiological parameters associated with the user 502 meeting a certain condition, for example, reaching a threshold. The certain condition can be pre-set by a system, or can be selected by a user, researcher, or in certain circumstances, by a professional (e.g., a therapist, nurse, or doctor). In some instances, the one or more physiological parameters associated with the user 502 include a brain wave associated with the user, heart rate associated with the user, a blood oxygen saturation associated with the user, and/or an amount of body movement associated with the user. In some instances, the body movement includes the movement of eye(s), hand(s), arm(s), head, foot/feet, leg(s), and/or torso of the user. In some instances, the one or more physiological parameters associated with the user 502 further include other physiological parameters that reflect the respiration state associated with the user 502 such as an airway flow rate associated with the user 502, an airway pressure associated with the user 502, and so on. In some instances, the one or more physiological parameters associated with the user 502 further includes a body temperature associated with the user 502, an ECG associated with the user 502, brain waves/activity associated with the user 502, a sound/noise level associated with the user 502, and so on.

The detection component 504 includes one or more sensors configured to sense the one or more physiological parameters associated with the user 502. For example, the one or more sensors can include an EEG, a heart rate sensor, an oxygen saturation sensor, and a body movement sensor. For example, the detection component 504 includes test probes and/or electrodes affixed to the user 502. In some instances, the one or more sensors may be integrated into the administration component 506. In some instances, detection component 504 further includes other types of sensors configured to detect physiological parameters that reflect the respiration state associated with the user 502 such as a flow rate sensor configured to detect an airway flow rate associated with the user 502, a pressure sensor configured to detect an airway pressure associated with the user 502, and so on. Additionally, the other types of sensors configured to detect physiological parameters that reflect the respiration state associated with the user 502 may be integrated into the administration component 506. In some instances, the detection component 504 further includes other types of sensors such as a body temperature sensor configured to detect a body temperature, a chest strap configured to detect ECG, a helmet or head worn device configured to detect brain waves/activity, a sound sensor configured to detect a sound/noise level associated with the user 502, and so on.

In some instances, the detection component 504 includes a wearable device that is attached to or worn by the user 502's body. For example, the wearable device includes a smartwatch, a smart bracelet, smart glasses, smart clothing, smart footwear, a smart armband, a smart belt, smart ring, smart earphone, a chest strap configured to detect a heart rate and/or ECG, a helmet configured to detect brain waveforms/activity, etc. In some instances, the one or more sensors are attached to or embedded in the wearable device. In some instances, the detection component 504 and the visualization component 508 may be integrated.

The administration component 506 is configured to administer a psychoactive substance to a respiratory system (e.g., the nose, the mouth, the respiratory tract, the lungs) of the user 502. The constituents of the psychoactive substance may refer to details described throughout this disclosure. The administration component 506 may have the same structure and function as the administration component 106 as described above with reference to FIG. 1. As an example, the administration component 506 administers a dose of 5 milligrams (mg) of cannabinoids to the user 502 upon receiving instructions from the terminal device 512.

The visualization component 508 is configured to present images and/or videos to the user 102. In implementations, the visualization component 508 may include visualization glasses, cellphones, etc. The audio component 510 is configured to provide audios to the user 102. In implementations, the audio component 510 may include earpieces, earbuds, earphones, headsets, headphones, audio amplifiers, speakers, and so on. In implementations, the visualization component 508 and the audio component 510 may be integrated.

The terminal device 512 is configured to receive triggers detected by the detection component 504. The terminal device 512 is further configured to send instructions to the administration component 506 to administer the psychoactive substance to a respiratory system (e.g., the nose, the mouth, the respiratory tract, the lungs) of the user 502. The terminal device 512 is further configured to control the visualization component 508 to present images and/or videos to the user 102. In implementations, the terminal device 122 may include a game station, a mobile phone, a tablet, a computer, a proprietary or purpose-built terminal, and so on. In some instances, the terminal device 512 and the visualization component 508 may be integrated.

As an example, the virtual/augmented environment provided by the system 500 may include game settings, where the user 502 may receive various feedbacks, such as visual feedback, auditory feedback, tactile feedback, and so on, when interacting with the game settings. The system 500 may also provide the user 102 with feedback by administering the psychoactive substance to the respiratory system of the user 102 based on the game settings (such as, buff and debuff effects) so as to make the game experience more realistic to the user 102. For example, when the user 102 in the game is hit by a magic in the game settings, the system 500 may administer the psychoactive substance to the respiratory system of the user 102 to alter the psychoactive state of the user 102. In implementations, the game settings may include, single player games, multiplayer games, online games, offline games, and so on. This disclosure is not limited thereto.

As another example, the virtual/augmented environment provided by the system 500 may include medical settings, where the user 502 may receive various feedbacks, such as visual feedback, auditory feedback, tactile feedback, and so on, when interacting with the medical settings. The system 500 may also provide the user 102 with feedbacks by administering the psychoactive substance to the respiratory system of the user 102 based on the medical settings. In implementations, the medical settings may include, behavior modification settings, trauma-focused therapeutic settings, psychotherapeutic settings, meditation settings, and so on. This disclosure is not limited thereto.

Figure 6:
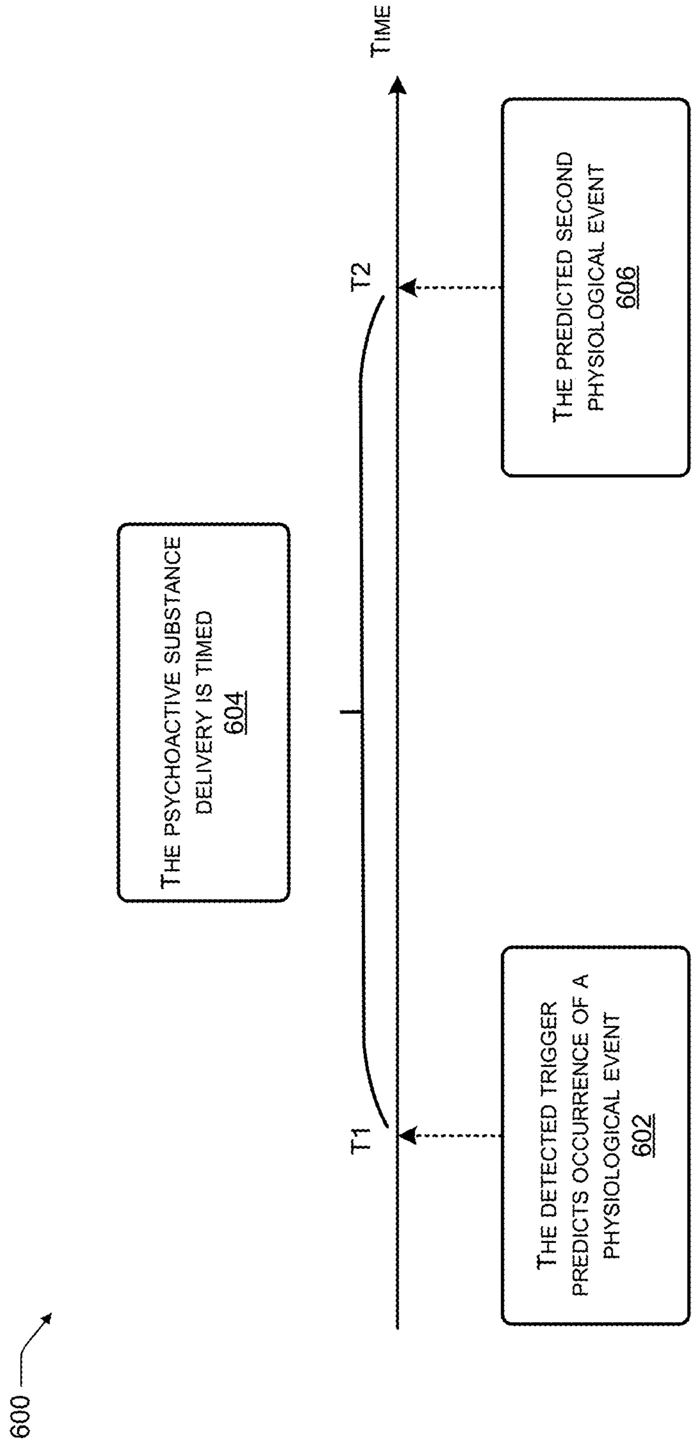
FIG. 6. illustrates an exemplary scenario where the detected trigger predicts the occurrence of a second physiological event, and the psychoactive substance delivery is timed so that it is effective at the time of the predicted second physiological event.

FIG. 6. illustrates an exemplary scenario 600 where the detected trigger predicts the occurrence of a second physiological event, and the psychoactive substance delivery is timed so that it is effective at the time of the predicted second physiological event.

Referring to FIG. 6, at 602, the detected trigger predicts occurrence of a physiological event. At 604, the psychoactive substance delivery is timed. At 606, the predicted second physiological event occurs. For example, the detected trigger predicts at a first time point T1 that the a second physiological event will occur on a second time point T2. Then, the psychoactive substance delivery is timed so that it is effective at the second time point T2 of the predicted second physiological event. Additional details are described throughout this disclosure.

(vii) EXEMPLARY EMBODIMENTS

1. A system for administering a psychoactive substance to a user, the system including:

a detecting component configured to detect a trigger associated with a user; and an administration component in communication with the detecting component, the administration component configured to administer a psychoactive substance to a respiratory system of the user based on a detected trigger, wherein the administration component includes:

a storage component configured to store the psychoactive substance; and a control component configured to administer the stored psychoactive substance in response to the detected trigger.

2. The system of embodiment 1, wherein the trigger is a sensed parameter meeting a condition.

3. The system of embodiment 2, wherein the sensed parameter includes a physiological parameter.

4. The system of embodiment 3, wherein the physiological parameter includes sleep.

5. The system of embodiment 4, wherein meeting the condition to detect the trigger includes detecting brain waves and brain signal patterns associated with REM sleep, non-REM sleep, sleep spindles, K-complexes, emotional content and respiratory disruptions.

6. The system of embodiment 4, wherein meeting the condition to detect the trigger includes detection of involuntary body movement, a minimum distance traveled from the location of sleep initiation, heart rate meeting a threshold; blood oxygen saturation meeting a threshold; respiration rate meeting a threshold; body temperature meeting a threshold; or skin galvanics meeting a threshold.

7. The system of embodiment 4, wherein the physiological parameter includes brain waves.

8. The system of embodiment 7, wherein meeting the condition to detect the trigger includes detecting alpha waves, beta waves, delta waves, gamma waves, or theta waves.

9. The system of embodiment 4, wherein the physiological parameter includes heart rate; blood oxygen saturation; respiration rate; body temperature; or skin galvanics.

10. The system of embodiment 9, wherein meeting the condition to detect the trigger includes heart rate meeting a threshold; blood oxygen saturation meeting a threshold; respiration rate meeting a threshold; body temperature meeting a threshold; or skin galvanics meeting a threshold.

11. The system of embodiment 2, wherein the sensed parameter includes location.

12. The system of embodiment 11, wherein the location includes a physical location or a virtual location.

13. The system of embodiment 11, wherein meeting the condition to detect the trigger includes detection of a location of a user in relation to a starting location; a distance traveled, or a velocity of movement.

14. The system of embodiment 2, wherein the sensed parameter includes movement.

15. The system of embodiment 14, wherein meeting the condition to detect the trigger includes detecting a distance traveled meeting a threshold or a velocity of movement meeting a threshold.

16. The system of embodiment 2, wherein the sensed parameter includes game play.

17. The system of embodiment 16, wherein the game play includes physical game play or virtual game play.

18. The system of embodiment 16, wherein meeting the condition to detect the trigger includes detecting a game event (e.g., running, jumping, floating, flying, swimming, falling, sleeping, dreaming, experiencing an injury, experiencing an adverse event, winning a contest of skill, winning a contest of chance, discovering buried treasure, powering-up, eating, copulating, meditating and/or dying).

19. The system of embodiment 2, wherein the sensed parameter includes activity of a brain-computer interface.

20. The system of embodiment 16, wherein meeting the condition to detect the trigger includes detection of a 5 to 10 minute time interval before a predicted P300 signal and subsequent BCI-initiated action.

21. The system of embodiment 2, wherein the sensed parameter includes ambient noise level.

22. The system of embodiment 19, wherein meeting the condition to detect the trigger includes detecting an ambient noise level that meets a threshold.

23. The system of embodiment 2, wherein the sensed parameter includes ambient light level.

24. The system of embodiment 21, wherein meeting the condition to detect the trigger includes detecting an ambient light level that meets a threshold.

25. The system of embodiment 2, wherein the sensed parameter includes air humidity.

26. The system of embodiment 23, wherein meeting the condition to detect the trigger includes detecting an air humidity level that meets a threshold.

27. The system of embodiment 2, wherein the sensed parameter includes ingestion of a beverage or food product.

28. The system of embodiment 2, wherein meeting the condition to detect the trigger includes detecting decreased alpha wave power and increased theta wave power associated with increased sleepiness and the automatically administered psychoactive substance includes gamma-aminobutyric acid (GABA), theanine, linalool, *Melissa officinalis* essential oil, delta-8 THC, delta-9 THC, delta-8 THC and delta-9 THC at a 1:1 ratio, and/or cannabis terpenes containing at least 1% linalool by mass of the entire terpene fraction and wherein the decreased alpha wave power and the increased theta wave power are in relation to the amplitude of alpha and theta waves exhibited while the user is alert.

29. The system of embodiment 2, wherein meeting the condition to detect the trigger includes detecting delta waves indicative of non-rapid eye movement (NREM) or slow wave sleep (SWS), and the automatically administered psychoactive substance includes *Valeriana officinalis* compounds, *Humulus lupulus* compounds, *Rosmarinus officinalis* essential oil, cannabidiol (CBD), delta-sleep-inducing peptide (DSIP), muramyl dipeptide (MDP), nitrous oxide (N20), gamma-hydroxybutyrate (GHB) or gabapentin.

30. The system of embodiment 2, wherein meeting the condition to detect the trigger includes detecting sleep spindles and the automatically administered psychoactive substance includes *Humulus lupulus* compounds, *Rosmarinus officinalis* essential oil, estrogen, progesterone or testosterone.

31. The system of embodiment 2, wherein meeting the condition to detect the trigger includes detecting K-complexes and the automatically administered psychoactive substance includes amphetamines.

32. The system of embodiment 2, wherein meeting the condition to detect the trigger includes detecting brain signal patterns associated with REM sleep and/or dream states and the automatically administered psychoactive substance includes galantamine compounds.

33. The system of embodiment 32, wherein the galantamine compounds include sesquiterpene lactones found in *Calea zacatechichi* or *Calea ternifolia.*

34. The system of embodiment 33, wherein the sesquiterpene lactones found in *Calea zacatechichi* or *Calea ternifolia* include Calaxin, Ciliarin, Calein A-F, Calealactones, or Caleachromenes.

35. The system of embodiment 2, wherein meeting the condition to detect the trigger includes detecting involuntary body movement of a user and the automatically administered psychoactive substance includes gamma-aminobutyric acid (GABA), theanine, linalool, *Melissa officinalis* essential oil, delta-8 THC, delta-9 THC, delta-8 THC and delta-9 THC at a 1:1 ratio, and/or cannabis terpenes containing at least 1% linalool by mass of the entire terpene fraction.

36. The system of embodiment 2, wherein meeting the condition to detect the trigger includes detecting beta waves and the automatically administered psychoactive substance includes oxygen, theobromine, caffeine, modafinil, or microdoses of amphetamines; or gamma-aminobutyric acid (GABA), theanine, linalool, *Melissa officinalis* essential oil (including phenolic compounds such as rosmarinic acid and caffeic acid derivatives), delta-8 THC, delta-9 THC, delta-8 THC and delta-9 THC at a 1:1 ratio, and/or cannabis terpenes containing at least 1% linalool by mass of the entire terpene fraction.

37. The system of embodiment 2, wherein meeting the condition to detect the trigger includes detecting event related potentials (ERPs) and the automatically administered psychoactive substance includes (i) methylphenidate or (ii) amphetamine plus dextroamphetamine.

38. The system of embodiment 37, wherein the ERP includes N100, P200, P300, ELAN, N400, or P600/SPS.

39. The system of embodiment 2, wherein meeting the condition to detect the trigger includes detecting A-HA brain signal patterns and the automatically administered psychoactive substance includes psilocybin, mescaline, LSD, DMT, 5MeO-DMT, or salvinorin.

40. The system of embodiment 2, wherein meeting the condition to detect the trigger includes detecting voluntary body movement of a user and the automatically administered psychoactive substance includes gamma-aminobutyric acid (GABA), theanine, linalool, *Melissa officinalis* essential oil, delta-8 THC, delta-9 THC, delta-8 THC and delta-9 THC at a 1:1 ratio, and/or cannabis terpenes containing at least 1% linalool by mass of the entire terpene fraction.

41. The system of embodiment 2, wherein meeting the condition to detect the trigger includes detecting heart rate meeting a threshold increase and associated activity in the central nucleus of the amydgala and the automatically administered psychoactive substance includes cannabidiol or benzodiazepines.

42. The system of embodiment 2, wherein meeting the condition to detect the trigger includes detecting blood oxygen saturation meeting a threshold, respiration rate meeting a threshold, body temperature meeting a threshold, or skin galvanics reaching a threshold and the automatically administered psychoactive substance includes tetrahydrocannabinol (THC) or oxytocin.

43. The system of embodiment 2, wherein meeting the condition to detect the trigger includes detecting an out of body experience (OBE) and the automatically administered psychoactive substance includes ketamine, *Salvia divinorum*, lysergic acid diethylamide (LSD) or 1-propionyl-lysergic acid diethylamide (1P-LSD).

44. The system of embodiment 43, wherein the *Salvia divinorum* includes salvinorin A.

45. The system of embodiment 2, wherein meeting the condition to detect the trigger includes detecting ingestion of a beverage or food product and the automatically administered psychoactive substance includes cocaine or an insulin inducer.

46. The system of embodiment 45, wherein the insulin inducer includes sucrose.

47. The system of embodiment 2, wherein meeting the condition to detect the trigger includes detecting gastric distress and the automatically administered psychoactive substance includes chamomile, ginger, licorice, mint or cannabigerol (CBG).

48. The system of embodiment 2, wherein meeting the condition to detect the trigger includes detecting an air humidity level surrounding the user below 30% and the automatically administered psychoactive substance includes shilajit.

49. The system of embodiment 2, wherein meeting the condition to detect the trigger includes detecting a sound level surrounding the user that falls below a threshold and the automatically administered psychoactive substance includes MSG.

50. The system of embodiment 2, wherein meeting the condition to detect the trigger includes detecting a sound level surrounding the user that exceeds a threshold and the automatically administered psychoactive substance includes GABA, theanine, or Withania somnifera (Ashwagandha)).

51. The system of embodiment 2, wherein meeting the condition to detect the trigger includes detecting a light level surrounding the user that falls below a lower threshold or exceeds an upper threshold and the automatically administered psychoactive substance includes melatonin, adenosine, or caffeine.

52. The system of embodiment 2, wherein the sensed parameter predicts occurrence of a physiological event and the administration component times the delivery of the psychoactive substance to pharmacokinetically align with the occurrence of the physiological event.

53. The system of embodiment 1, wherein the psychoactive substance includes a constituent extracted or derived from a plant, fungi, or animal belonging to the genus of *Acacia, Alchornea, Amanita, Amsonia, Anadenanthera, Apocynum, Areca, Argyreia, Artemisia, Arundo, Aspidosperma, Banisteriopsis, Burkea, Calea, Calligonum, Calycanthus, Cannabis, Catha, Carex, Claviceps, Copelandia, Datura, Delosperma, Desfontainia, Desmanthus, Desmodium, Dictyoloma, Diplopterys, Dutaillyea, Echinopsis, Elaeagnus, Erigonum, Erythroxylum, Festuca, Glycyrrhiza, Guiera, Gymnacranthera, Hammada, Heimia, Horsfieldia, Humulus, Ilex, Ipomoea, Iryanthera, Leonotis, Leptactinia, Lespedeza, Limonia, Lolium, Lophophora, Matricaria, Meconopsis, Melicope, Melissa, Mentha, Mimosa, Mitragyna, Mucuna, Nectandra, Newbouldia, Nicotiana, Nymphaea, Opuntia, Osteophloem, Panaeolus, Pandanus, Papaver, Passiflora, Pauridiantha, Peganum, Petalostylis, Phalaris, Phyllodium, Phyllomedusa, Picrasma, Pilocarpus, Plectocomiopsis, Prosopis, Psilocybe, Psychotria, Punica,*

*Rhinella, Rivea, Rosmarinus, Salvia, Shepherdia, Simira, Strychnos, Tabernaemontana, Tabernanthe, Testulea, Tetradium, Trachelospermum, Tribulus, Uncaria, Urtica, Valeriana, Vepris, Vestia, Vinca, Virola, Voacanga, Withania, Zanthoxylum, Zingiber* and *Zygophyllum*.

54. The system of embodiment 1, wherein the psychoactive substance includes a synthetic, semisynthetic, and/or a purified version of a constituent extracted or derived from a plant belonging to the genus of *Cannabis*, wherein the constituent includes cannabinoid, terpenoid, and/or flavonoid compounds.

55. The system of embodiment 1, wherein the psychoactive substance includes one or more of tetrahydrocannabinol (THC), tetrahydrocannabinolic acid (THCA), cannabidiol (CBD), cannabidiolic acid (CBDA), cannabinol (CBN), Cannabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin (CBCV), cannabigerovarin (CBGV), cannabigerol monomethyl ether (CBGM), cannabielsoin (CBE), and/or cannabicitran (CBT).

56. The system of embodiment 1, wherein the psychoactive substance includes a compound in the following chemical classes: arylcyclohexylamines, beta-carbolines, cathinones, ergolines, indole alkaloids, lysergamides, methylxanthine alkaloids, muscimol and precursors thereof, phenethylamines, salvinorins, tryptamines, and/or *Phyllomedusa* peptides.

57. The system of embodiment 1, wherein the psychoactive substance includes a compound or a formulation that exhibits central nervous system (CNS) activity at adenosinergic, adrenergic, cannabinergic, dopaminergic, gamma-Aminobutyric acid (GABA), N-methyl-D-aspartate (NMDA), norepinephrine, and/or serotoninergic including 5-hydroxytryptamine 2A (5-HT2A) and 5-hydroxy-tryptamine 1A (5-HT1A) receptors.

58. The system of embodiment 1, wherein the psychoactive substance includes ketamine and/or galantamine.

59. The system of embodiment 1, wherein the administration component is further configured to administer the psychoactive substance to the respiratory system of the user based on a dosing schedule.

60. The system of embodiment 1, wherein the administration component further includes:

an airway component configured to provide an airflow to the respiratory system of the user; and an introducing component in fluid communication with the airway component, the introducing component being configured to introduce the stored psychoactive substance into the airflow.

61. The system of embodiment 33, wherein the introducing component is further configured to introduce the psychoactive substance into the airflow in a vaporized form, in droplets, and/or in an aerosolized form.

62. The system of embodiment 32, wherein the dosing schedule includes a dose of the psychoactive substance to be administered and timing to administer the dose of the psychoactive substance.

63. The system of embodiment 1, wherein the trigger includes whether a physiological parameter is above, equal to, or below a threshold.

64. The system of embodiment 1, further including a terminal device in communication with the detection component and the administration component, the terminal device being configured to:

display, via a user interface and a dosing schedule;

receive, via the user interface, one or more additional dosing schedules; and send data associated with the one or more additional dosing schedules to the administration component.

65. The system of embodiment 1, wherein the detection component includes a wearable device.

66. The system of embodiment 38, wherein the wearable device includes a smart watch, bracelet, glasses, clothing, footwear, armband, belt, ring, earphone, chest strap, helmet, cap, or headband.

As used herein, "pharmacokinetically align" means that the intended physiological activity of the psychoactive substance will have begun when the trigger-predicted physiological event occurs. Particular examples of predictive triggers are provided in Tables 1, 2, and 3. Additional predictive triggers and predicted physiological events include: sleep theta waves predict REM sleep (with a time delay of 90 minutes for the first sleep cycle of the night); reduction in beta power of 15-25 Hz above the parieto-occipital and centro-temporal regions up to eight seconds predicts insight (with a time delay of 8 seconds); K-complex density predicts sleep apnea event (with a time delay of 0 seconds); the P300 ERP signal predicts object recognition (with a time delay of 250 ms).

(viii) CLOSING PARAGRAPHS

As will be understood by one of ordinary skill in the art, each embodiment disclosed herein can comprise, consist essentially of or consist of its particular stated element, step, ingredient, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; ±16% of the stated value; 15% of the stated value; ±14% of the stated value; 13% of the stated value; ±12% of the stated value; 11% of the stated value; 10% of the stated value; 9% of the stated value; 8% of the stated value; 7% of the stated value; ±6% of the stated value; 5% of the stated value; 4% of the stated value; 3% of the stated value; 2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it is individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member is referred to and claimed individually or in any combination with other members of the group or other elements found herein. It is anticipated that one or more members of a group are included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

It is to be understood that the embodiments of the disclosure disclosed herein are illustrative of the principles of the present disclosure. Other modifications that are employed are within the scope of the disclosure. Thus, by way of example, but not of limitation, alternative configurations of the present disclosure are utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure are embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

Further, the processes discussed herein are implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skills in the art will readily recognize that certain steps or operations illustrated in the figures above are eliminated, combined, or performed in an alternate order. Any steps or operations are performed serially or in parallel (unless the context requires one or the other). Furthermore, the order in which the operations are described is not intended to be construed as a limitation.

Embodiments are provided as a software program or computer program product including a non-transitory computer-readable storage medium having stored thereon instructions (in compressed or uncompressed form) that are used to program a computer (or other electronic device) to perform processes or methods described herein. The computer-readable storage medium is one or more of an electronic storage medium, a magnetic storage medium, an optical storage medium, a quantum storage medium, and so forth. For example, the computer-readable storage media includes hard drives, floppy diskettes, optical disks, ROMs, RAMs, EPROMs, EEPROMs, flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of machine-readable signals, whether modulated using a carrier or unmodulated, can include signals that a computer system or machine hosting or running a computer program can be configured to access, including signals transferred by one or more networks. For example, the transitory machine-readable signal may include transmission of software by the Internet. Systems and components described with reference to FIGS. 1A, 1B, and 1C such as the detection component 104, the administration component 106, and/or the terminal device 122 may include some or all of these types of computer-readable storage media to perform the various acts and operations described herein.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skills in the art.

Additionally, those having ordinary skills in the art readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

Those of ordinary skill in the art will recognize in light of the present disclosure that many changes can be made to the specific embodiments disclosed herein and still obtain a like or similar result without departing from the spirit and scope of the disclosure.

What is claimed is:

1. A system for automatically administering a psychoactive substance to an airway of a user during sleep, the system comprising:

one or more sensors configured to detect at least one trigger associated with the user during the sleep; and an airflow distributor in communication with the one or more sensors, the airflow distributor automatically administering the psychoactive substance to the airway of the user based on the detected trigger, wherein the airflow distributor comprises:

a storage storing at least one dose of the psychoactive substance; and a controller automatically administering a dose of the stored psychoactive substance to the airway of the user in response to the detected trigger, wherein the detected trigger is brain signal patterns associated with REM sleep and the automatically administered dose of the psychoactive substance comprises galantamine or lucid dreaming inducing compounds;

the detected at least one trigger is an air humidity level surrounding the user below 30% and the automatically administered dose of the psychoactive substance comprises shilajit;

the detected at least one trigger is sleep spindles and the automatically administered dose of the psychoactive substance comprises *Humulus lupulus* compounds, *Rosmarinus officinalis* essential oil, estrogen, progesterone or testosterone;

the detected at least one trigger is decreased alpha wave power and increased theta wave power and the automatically administered dose of the psychoactive substance comprises gamma-aminobutyric acid (GABA), theanine, linalool, *Melissa officinalis* essential oil, delta-8 THC, delta-9 THC, delta-8 THC and delta-9 THC at a 1:1 ratio, or cannabis terpenes containing at least 1% linalool by mass of the entire terpene fraction and wherein the decreased alpha wave power and the increased theta wave power are in relation to the amplitude of alpha and theta waves exhibited by the user while the user is alert;

the detected at least one trigger is delta waves, and the automatically administered dose of the psychoactive substance comprises *Rosmarinus officinalis* essential oil, cannabidiol (CBD), delta-sleep-inducing peptide (DSIP), muramyl dipeptide (MDP), nitrous oxide (N20), gamma-hydroxybutyrate (GHB) or gabapentin;

the detected at least one trigger is K-complexes and the automatically administered dose of the psychoactive substance comprises amphetamines;

the detected at least one trigger is a heart rate of the user meeting a threshold increase and the automatically administered dose of the psychoactive substance comprises cannabidiol or benzodiazepines; and/or the detected at least one trigger is a light level surrounding the user that falls below a lower threshold or exceeds an upper threshold and the automatically administered dose of the psychoactive substance comprises, melatonin, adenosine, or caffeine.

2. The system of claim 1, wherein the lucid dreaming inducing compounds comprise sesquiterpene lactones found in *Calea zacatechichi* or *Calea ternifolia*.

3. The system of claim 2, wherein the sesquiterpene lactones found in *Calea zacatechichi* or *Calea ternifolia* comprise Calaxin, Ciliarin, Calein A-F, Calealactones, or Caleachromenes.

4. The system of claim 1, wherein the one or more sensors are part of a wearable device.

5. The system of claim 4, wherein the wearable device comprises a smart watch, bracelet, glasses, clothing, footwear, armband, belt, ring, earphone, chest strap, helmet, cap, or headband.

6. A system for automatically administering a psychoactive substance to an airway of a user during sleep, the system comprising:

one or more sensors configured to detect a trigger associated with the user during the sleep wherein the detected trigger predicts an occurrence of a physiological event during the sleep; and an airflow distributor in communication with the one or more sensors, the airflow distributor automatically administering the psychoactive substance to the airway of the user based on the detected trigger, wherein the airflow distributor comprises:

a storage storing at least one dose of the psychoactive substance; and a controller automatically administering a dose of the stored psychoactive substance to the airway of the user to achieve a pharmacodynamic effect at a time coinciding with the predicted occurrence of the physiological event during the sleep in response to the detected trigger.

7. The system of claim 6, wherein the psychoactive substance comprises one or more of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin (CBCV), cannabigerovarin (CBGV), cannabigerol monomethyl ether (CBGM), cannabielsoin (CBE), and cannabicitran (CBT).

8. The system of claim 6, wherein the physiological event is different than the detected trigger.

9. The system of claim 8, wherein a dosing schedule comprises the dose of the psychoactive substance to be administered and timing to administer the dose of the psychoactive substance.

10. The system of claim 6, wherein the airflow distributor further comprises:

an airflow provisioner configured to provide an airflow to the respiratory system of the user; and an airflow communicator in fluid communication with the airflow provisioner, the airflow communicator being configured to introduce the stored psychoactive substance into the airflow of the user's respiratory system.

11. The system of claim 10, wherein the airflow communicator is further configured to introduce the psychoactive substance into the airflow of the user's airway in a vaporized form, in droplets, and/or in an aerosolized form.

12. The system of claim 6, further comprising a terminal device in communication with the one or more sensors and the airflow distributor, the terminal device being configured to:

display, via a user interface a dosing schedule;

receive, via the user interface, one or more additional dosing schedules; and send data associated with the one or more additional dosing schedules to the airflow distributor.

13. A system for automatically administering galantamine to a nasal passage of a user thirty to forty-five minutes before a predicted 5/6 rapid eye movement (REM) sleep cycle of the user, the system comprising:

one or more sensors configured to detect the thirty to forty-five minute time interval before the predicted onset of the 5/6 rapid eye movement (REM) sleep cycle; and an airflow distributor in communication with the one or more sensors, the airflow distributor administering the galantamine to the nasal passage of the user based on the time interval, wherein the airflow distributor comprises:

a storage storing at least one dose of the galantamine; and a controller automatically administering a dose of the stored galantamine to the nasal passage of the user in response to the detected time interval.

* * * * *